(12) United States Patent
Dzeng et al.

(10) Patent No.: US 7,758,623 B2
(45) Date of Patent: Jul. 20, 2010

(54) TRANSESOPHAGEAL HEAT EXCHANGE CATHETER FOR COOLING OF THE HEART

(75) Inventors: Elizabeth Dzeng, Baltimore, MD (US); Fay Xing, Palo Alto, CA (US); Jessica March, Philadelphia, PA (US); Muhammad Rijwane-ul Islam, Santa Clara, CA (US); Raphael Michel, San Diego, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1304 days.

(21) Appl. No.: 10/803,235

(22) Filed: Mar. 17, 2004

(65) Prior Publication Data

US 2004/0210281 A1 Oct. 21, 2004

(51) Int. Cl.
*A61F 7/12* (2006.01)
(52) U.S. Cl. ........................... 607/105; 607/104
(58) Field of Classification Search ............. 606/20–23; 607/104–107
See application file for complete search history.

(56) References Cited

U.S. PATENT DOCUMENTS

| | | | |
|---|---|---|---|
| 3,425,419 A | | 2/1969 | Dale |
| 5,409,006 A * | | 4/1995 | Buchholtz et al. ........... 600/439 |
| 5,531,776 A * | | 7/1996 | Ward et al. .................. 607/105 |
| 5,624,392 A * | | 4/1997 | Saab ........................... 604/43 |
| 5,716,386 A * | | 2/1998 | Ward et al. .................. 607/106 |
| 5,868,735 A * | | 2/1999 | Lafontaine ................... 606/21 |
| 5,971,979 A * | | 10/1999 | Joye et al. ..................... 606/21 |
| 6,068,653 A * | | 5/2000 | LaFontaine ................. 607/116 |
| 6,148,222 A | | 11/2000 | Ramsey |
| 6,231,594 B1 * | | 5/2001 | Dae ............................ 607/96 |
| 6,283,959 B1 * | | 9/2001 | Lalonde et al. .............. 606/21 |
| 6,427,089 B1 * | | 7/2002 | Knowlton .................. 607/101 |
| 6,690,578 B2 | | 2/2004 | Edelmann |
| 6,726,653 B2 * | | 4/2004 | Noda et al. ................. 604/113 |
| 7,077,825 B1 * | | 7/2006 | Stull ........................... 604/113 |
| 7,144,407 B1 * | | 12/2006 | Lasersohn .................. 606/192 |
| 2002/0032438 A1 * | | 3/2002 | Lafontaine ................... 606/21 |

OTHER PUBLICATIONS

Simon R. Dixon et al., J. Am. Coll. Cardiol., 2002, pp. 1928-1934, vol. 40(11).
Dae et al., Am. J. Physiol. Heart Circ. Physiol., 2002, pp. H1584-H1591, vol. 282.
Krijenen et al., J. Clin. Pathol., 2002, pp. 801-811, vol. 55(11).
Yellon and Baxter, Heart, 2000, pp. 381-387, vol. 83(4).
Curtis and Trezek, Heat Transfer in Medicine and Biology, 1995, pp. 261-286, vol. 2, Plenum Publishing Corp., New York, NY.

* cited by examiner

*Primary Examiner*—Roy D Gibson
(74) *Attorney, Agent, or Firm*—Bell & Associates; Matthew R. Kaser; Adam W. Bell

(57) ABSTRACT

The present invention encompasses a heat exchange catheter for indirect cooling of internal organs, particularly the heart. The heat exchange catheter is inserted into the esophagus and a cooled fluid is circulated within the catheter, cooling the esophagus, and by conduction, the heart. The heat exchange catheter or the invention may be rapidly deployed in the field and is particularly useful for preventing and reducing tissue damage caused by ischemia.

19 Claims, 14 Drawing Sheets

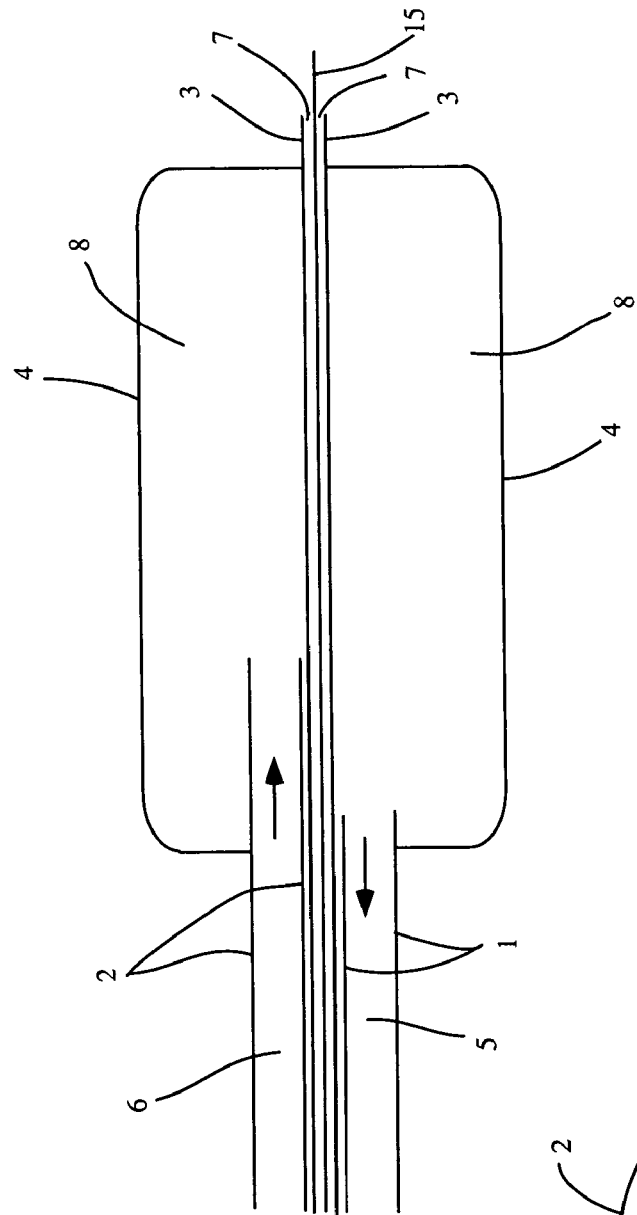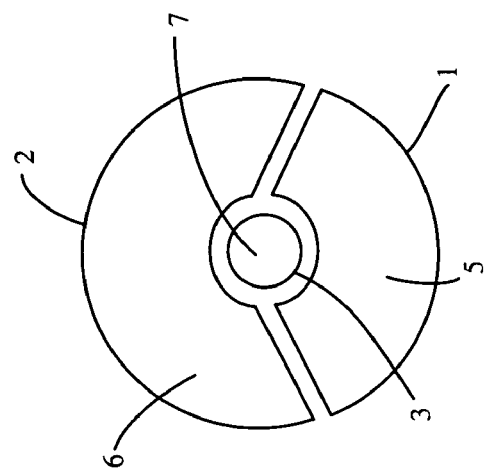
Fig. 6A
Fig. 6B

TRANSESOPHAGEAL HEAT EXCHANGE CATHETER FOR COOLING OF THE HEART

The present application claims the benefit of U.S. Provisional Patent Application Ser. No. 60/455,518 entitled TRANSESOPHAGEAL COOLING OF THE HEART, filed Mar. 17, 2003, which is herein incorporated by reference in its entirety for all purposes.

FIELD OF THE INVENTION

The present invention relates to devices and methods used to cool internal organs; more specifically to devices and methods used to cool the ischemic heart.

1. Background

Protection of ischemic myocardium has long been the focus of many research scientists. Cardiomyocytes have roughly thirty minutes after the onset of total coronary artery occlusion before they go into irreversible cell death and subsequent scarring. The earlier blood flow is established, either by angioplasty or thrombolytic therapy, the better the prognosis. However, in the United States, only about two-thirds of patients with acute myocardial infarction (AMI) receive reperfusion therapy. Of those who do, the time to coronary artery reperfusion can average nearly three hours after the onset of chest pain. Therefore there is a clear need for an effective method to protect ischemic myocardium and to delay cell death.

The protective benefits of hypothermia, or organ cooling, particularly in cardiology and neurology have been known for about fifty years. By slowing blood flow through major organs, cold therapy can protect organs such as the brain and heart from stroke and myocardial infarction. Several studies have suggested that there is a correlation between body, blood and pericardial temperatures with myocardial infarct size. A number of studies have also shown that cooling of the heart myocardium immediately after the onset of ischemia has protective functions on the cardiac tissue. (See, for example, Dixon et al. (2002) J. Am. Coll. Cardiol., 40:1928-1934; Dae et al. (2002) Am. J. Physiol. Heart Circ. Physiol., 282: H1584-H1591). Although the mechanism of protection is not fully determined, one possibility is a reduction in high energy phosphate utilization in the myocardium. This can occur in the risk region itself, or be due to reduced contractility (and metabolic demand) in the border zone. The correlation between myocardial temperature and the progression of necrosis suggests the potential use of hypothermia as a therapeutic maneuver to protect regionally ischemic myocardium.

In addition to decreasing metabolic demands to myocardial cells during infarction, another motivation for pursuing cooling therapy is to minimize reperfusion injury caused by thrombolytic drugs. Although thrombolytic drugs are the prerequisite for tissue salvage during AMI, they pose the danger of additional myocardial injury. Several studies have shown that a distinct form of cell death, namely apoptosis, occurs during reperfusion. (See, for example, Krijnen et al., (2002) J. Clin. Pathol., 55:801-811; Schofield and Hill, (2001) Am. J. Cardiovasc. Drugs, 1:23-25; Yellon and Baxter, (2000) Heart, 83:381-387.)

There is a clear need for finding agents that protect myocardium from reperfusional injury. Various agents such as apoptotic pathway inhibitors, and antioxidants have undergone preclinical evaluation. Tissue cooling, interestingly enough, has also shown by various research studies to have protective effects on reperfusional injury.

Therapeutic hypothermia was first used in neurosurgical patients by Temple Fay in the 1940s. Bigelow pioneered the use of deep hypothermia to protect the brain during experimental cardiac surgery in the early 1950s. During the 1960s, there was an explosion of interest in the use of moderate and deep hypothermia during aneurysm, spinal cord and cardiac surgery, as well as in the management of neurotrauma. Deep cooling has been used by cardiologists in cases where slowed organ function or blood flow is considered essential. However, broader applications and protective benefits of cooling have largely been limited due to complications associated with deep hypothermia such as cardiac irritability, pulmonary infections, and coagulopathies.

In the late 1980s and early 1990s, there was an increasing body of evidence demonstrating the value of mild hypothermia. A number of studies have consistently shown that mild hypothermia (32-35° C.) attenuates hypoxic-ischemic brain and cardiac injury in animal models, and some preliminary human studies have suggested similar protection. As a result, the utilization of mild hypothermia as a therapeutic maneuver following ischemic injury poses promising potential. Before this intervention can be used clinically, improved techniques must be developed to reduce the temperature of the myocardium.

Historical approaches to cooling such as ice and saline flushes are often messy, slow, and unpredictable in practice. In larger animals it takes several hours to lower core temperature by cooling the entire body topically. More recently, cooling technologies have been developed that employ a catheter filled with flowing saline through which heat exchange occurs. No fluid is physically removed or added to the blood flow. A device that can cool the heart quickly, locally, and efficiently is needed.

2. Current State of the Art

Surface cooling is currently the most common cooling method employed in the clinical setting. Cooling, maintenance, and reversal of hypothermia is generally achieved through the use of convective air blankets, water mattresses, alcohol bathing, and ice packing. There are clear disadvantages and difficulties to these methods including significant patient discomfort, difficulty of administration, and increased nursing time and labor.

Several companies are currently pursuing more efficient and comfortable means of cooling. Though myocardial infarction remains the most significant clinical application for this therapy, other applications include ischemic stroke, head injury, cerebral aneurysm surgery, and for brain protection after cardiac arrest. Many companies have developed a catheter that can be placed in the inferior vena cava using standard catheter insertion techniques through the femoral artery.

For example, Innercool's CELSIUS CONTROL SYSTEM™ uses a flexible temperature control element that is cooled or warmed with saline solution circulating in a closed loop. No blood is circulated outside the body nor is there any fluid infused into the patient. The average cool-down rate is 5.0-6.0° C./hour and the re-warm rate is 2.0-3.0° C./hour. Target temperatures to achieve mild hypothermia are about 32-33° C.

In another example, Radiant Medical is pursuing the Reprive ENDOVASCULAR TEMPERATURE THERAPY (ETT)™ system to cool the blood to 33° C. and to warm it. Two similar devices are being developed using this system: COOL MI™ for acute myocardial infarctions and COOL AID™ for acute ischemic stroke. (The ETT™ system consists of four components: a central venous heat exchange catheter, a heat exchange cassette, single use temperature probes, and a control unit. All but the control unit are single use devices. This system can also be used to maintain blood temperature, which can be beneficial in surgeries and in the neurological intensive care unit.

Although these technologies are a step above surface cooling techniques, there are still major disadvantages. These technologies cool the entire body by inserting a catheter into the inferior vena cava. Cooling the entire body as a means of cooling the heart is energetically inefficient and more time consuming. Another problem is severe shivering in the patient when blankets are changed. A method to specifically cool the heart would be a more elegant solution.

Such specific cooling might also increase the speed with which the blood can be cooled. In a myocardial infarction, cell death of the cardiac cells increase with prolonged ischemia due to reduced blood flow of oxygenated blood. By increasing the rate at which the tissue temperature decreases and therefore slowing the cells' metabolism, more cells will live through an ischemic event.

Other companies are exploring cooling and/or temperature controlling mechanisms but for different applications. For example, Cardeon is pursuing cooling technology in neurological diseases such as stroke. They hope to preserve neurological integrity and limit neurological complications by TARGETED CIRCULATORY MANAGEMENT™. This includes tailoring the cerebral, corporeal, and cardiac environment through regional segmentation of temperature, flow, and perfusate composition.

In another example, CryoCor is using cooling technologies to create circumferential pulmonary vein lesions that treat atrial fibrillation. Their proprietary system uses cold energy to create lesions in the cardiac tissue that become electrically isolated from the remainder of the heart. This cold energy destroys the tissue responsible for the initiation or maintenance of arrhythmias. The CryoCor CARDIAC CRYOABLATION™ system delivers extreme cold from the catheter tip. The catheter features steering capabilities, a pressure monitoring tip, a cardiac electrical signal recorder, and three quick-connect receptacles providing refrigerant gas.

BRIEF DESCRIPTION OF THE DRAWINGS

FIG. 6A shows a longitudinal cross-section of an alternative exemplary embodiment of the invention. Direction of flow is shown by the arrows.

FIG. 6B shows a lateral cross-section of the proximal end of the alternative exemplary embodiment of the invention.

BRIEF DESCRIPTION OF THE INVENTION

Figure 1:
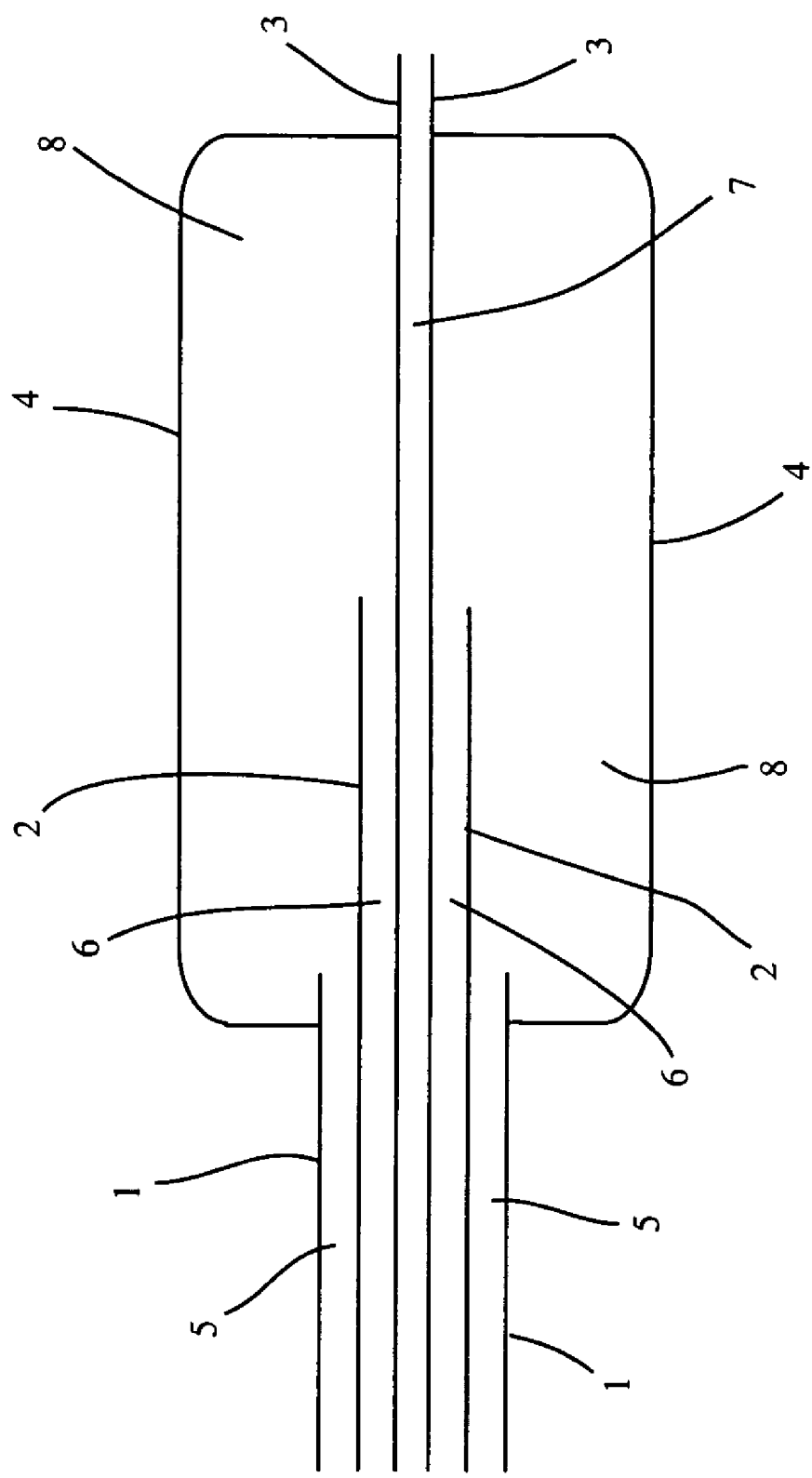
FIG. 1 shows a longitudinal cross-section of an exemplary embodiment of the invention.

The present invention encompasses a heat exchange catheter for indirect cooling of a target organ, such as the heart. The heat exchange catheter may be inserted into an anatomical structure adjacent to the target organ, removing heat from the wall tissue of the anatomical structure, and thereby indirectly cooling the target organ. The target organ can be the heart but is not limited to that tissue. The anatomical structure can be the esophagus but is not limited to that structure. The target organ may be cooled at a rate of between about 0.5° C./hour and 30° C./hour, or about 1.0° C./hour and 20° C./hour, or about 2.0° C./hour and 10° C./hour, preferably at a rate of about 3° C./hour to about 5° C./hour. The target organ also may be cooled by at a rate of between about 0.5° C./30 minutes and 30° C./30 minutes, or about 1.0° C./30 minutes and 20° C./30 minutes, or about 2.0° C./30 minutes and 10° C./30 minutes, preferably at a rate of about 2° C./30 minutes to about 5° C./30 minutes.

The invention provides a heat exchange catheter adapted for placement within an anatomical structure of a mammalian subject, wherein the heat exchange catheter effects in situ heat exchange between the heat exchange catheter and the anatomical structure, thereby altering the temperature of a target tissue or region in contact with the anatomical structure. The heat exchange catheter comprises: (a) a first elongate tubular body 1 having a first proximal end and a first distal end; (b) a second elongate tubular body 2 disposed longitudinally within the first elongate tubular body 1 having a second proximal end and a second distal end; and (c) a balloon 4 in fluid communication with the first elongate tubular body 1 and the second elongate tubular body 2. The balloon is affixed to the outer surface of the first elongate tubular body in proximity to the distal end. The balloon has an outer surface and an inner surface and is adapted to conform in shape to the anatomical structure, such that when inflated, the outer surface of the balloon is in contact with a surface of the anatomical structure and forms a heat exchange surface with the surface of the anatomical structure. The inner surface of the balloon forms a heat exchange surface with a thermal exchange composition within the balloon. The material of the balloon conducts heat such that heat is conducted from one heat exchange surface to the other.

In use the heat exchange catheter is inserted into the lumen of an anatomical structure such as the esophagus. A thermal exchange composition is pumped through one of the elongate tubular bodies into the balloon. The balloon expands filling the lumen of an anatomical structure and cooling the surrounding tissue and any tissue that may be in contact with this tissue. The thermal exchange composition exits the balloon via another of the elongate tubular bodies and in some embodiments, may be cooled and re-circulated. The thermal exchange composition may be a solid composition, a gel, a liquid, and a gas suitable for transferring heat energy. Changing the temperature of the thermal exchange composition or altering its flow rate alters the temperature of the target region. A pump may be employed to circulate the fluid in the catheter tubular bodies, and the fluid flow rate can be regulated by adjusting the pumping rate.

The heat exchange catheter may be used to cool the myocardium of the heart by inserting the device into the esophagus. Alternately, the anatomical structure into which the heat exchange catheter is placed may be for example, the esophagus, the oral cavity, the nasopharyngeal cavity, the auditory tube and tympanic cavity, the sinus of the brain, the arterial system, the venous system, the larynx, the trachea, the bronchus, the stomach, the duodenum, the ileum, the colon, the rectum, the bladder, the ureter, the ejaculatory duct, the vas deferens, the urethra, the uterine cavity, the vaginal canal, and the cervical canal. The heat exchange catheter may be used both for cooling and for heating a target organ.

The heat exchange catheter may additionally include a third elongate tubular body 3 having a third proximal end and a third distal end; and (d) a balloon 4 in fluid communication with the first elongate tubular body 1 and the second elongate tubular body 2. The balloon is firstly affixed to the outer surface of the first elongate tubular body in proximity to the distal end, and secondly affixed to the outer surface of the third elongate tubular body in proximity to the distal end.

The heat exchange catheter may additionally include a transducer 29 (which may also be called a sensor or probe) for example an ultrasound visualizing transducer. A transducer may be any device that measures a physical or physiological parameter such as temperature, pressure, electromagnetic fluctuations or sound that may be used in clinical monitoring of cardiac function, for example for monitoring the movement of the septal wall. The transducer 29 may be affixed, for example, to the distal end of the third elongated tubular body 3. The transducer may be used to detect very early wall motion abnormalities associated with ischemia and may further be used to locate the position of the catheter inside the esophagus in relation to the heart as well as to determine the location of the ischemia.

The heat exchange catheter may additionally include a guidewire 15 disposed longitudinally within the third elongate tubular body, the guidewire having a proximal end and a distal end. Additionally, a guide sheath may be fitted over at least a portion of the first elongate tubular body, the guide sheath having a proximal end and a distal end. In some embodiments, the present invention may include a digestible composition 30 affixed to the distal end of the guidewire 15 to facilitate placement of the guidewire in the esophagus. The digestible composition attached to the guidewire is placed in the mouth of the subject, the subject swallows the digestible composition, thereby bringing the guidewire into placement in the esophagus.

In various embodiments the first and second elongate tubular bodies may not be concentric, but may be separate and independent. In some embodiments the tubular bodies may be of different cross-sectional areas. In other embodiments, the heat exchange catheter possesses only a first elongate tubular body and a second elongate tubular body, but does not possess a third first elongate tubular body. In such embodiments, the balloon is attached only to the outer surface of the first elongated tubular body and can be inflated by pumping a fluid such as a heat exchange composition through the second elongate tubular body which is disposed concentrically within the first elongate tubular body. The fluid enters the balloon, inflating it, and exits out through the first elongate tubular body.

In a specific embodiment, the heat exchange catheter is adapted for insertion of the esophagus and may be used to cool the heart. The esophagus is anatomically positioned adjacent to the posterior part of the heart. In particular the posterior myocardium of the left ventricle, the posterior myocardium of the right ventricle, and the posterior myocardium of the left auricle are each adjacent to the anterior wall of the esophagus. Using the heat exchange catheter as disclosed the anterior wall of the esophagus can be cooled, heat is thereby conducted from the heart, resulting in cooling of the heart myocardium.

In an alternate embodiment, cooling of the heart may be achieved by inserting the device into the esophagus and then, from the inside, puncturing the esophagus using a catheter tubular body and extending the catheter perpendicularly to and through the wall of the esophagus towards the left ventricle in the thoracic cavity. The balloon may be shaped to form a surrounding shape that surrounds the thoracic cavity-facing wall of the left ventricle. The balloon is inflated and the thermal transfer composition is circulated within the balloon to cool the heart.

In an further alternative embodiment, a catheter is extended through the wall of the esophagus into the thoracic cavity as disclosed above, and a coolant is pumped through a first tubular body directly into the thoracic cavity between the left ventricle and the esophagus (not into a balloon). A second tubular body is in fluid communication with the cavity and conducts the coolant away from the tissue.

It is believed that transesophageal cooling of the heart is an entirely novel concept, and in its simplest embodiment the invention encompasses a device for transesophageal cooling of the heart of a subject comprising: a reservoir adapted in shape and size to conform to the lumen of the esophagus, and a thermal exchange composition disposed within the reservoir. The device may optionally include one or more tubes in fluid communication with the balloon. These tubes may be used to transmit the thermal exchange composition into and out of the balloon. The thermal exchange composition may be pumped through the tubes and the balloon using a conventional pump, generally present at the proximal end of the tubes, outside the patient being treated. Alternatively, the thermal exchange composition may not be circulated, but may be contained statically within the balloon.

Another embodiment of the invention is a heat exchange catheter system for cooling a target organ, the heat exchange catheter comprising an inflatable saccular body defining a lumen, adapted to conform in shape and size to the interior of the anatomical structure. "Saccular body" refers to an flexible saclike structure which may be sealed or may have an opening. In certain embodiments the saccular structure may be a balloon. When placed within the anatomical structure and inflated, the outer surface of the saccular body is at least partially in contact with the inner surface of the anatomical structure providing a heat exchange surface by which heat is exchanged between the anatomical structure and interior of the inflatable saccular body, thereby cooling a target organ adjacent to the anatomical structure. One or two elongate tubular bodies may optionally be sealably affixed to the outer surface of the first elongate tubular body, these tubes may be used to conduct a thermal exchange composition through the inflatable saccular body.

The invention also includes methods for altering the temperature of a target organ such as the myocardium of the heart. Such methods include a method for altering the temperature of the myocardium of the heart in a subject, the method comprising the steps of: (a) providing a thermal exchange composition, and (b) placing the thermal exchange composition within the esophagus of the subject, whereby the myocardium of the heart is cooled. In such methods, the thermal exchange composition is optionally contained within a reservoir. The reservoir may comprise a balloon shaped and sized to fit within the lumen of the esophagus. Such methods include a method where the thermal exchange composition is contained within the heat exchange catheter system described herein. Using such methods, the temperature of the myocardium of the heart may be altered at a rate of between about 0.5° C./hour and 30° C./hour, or about 1.0° C./hour and 20° C./hour, or about 2.0° C./hour and 10° C./hour, preferably at a rate of about 3° C./hour to about 5° C./hour. The target organ also may be cooled by at a rate of between about 0.5° C./30 minutes and 30° C./30 minutes, or about 1.0° C./30 minutes and 20° C./30 minutes, or about 2.0° C./30 minutes and 10° C./30 minutes, preferably at a rate of about 2° C./30 minutes to about 5° C./30 minutes.

The ease of use and speed of deployment of the heat exchange catheter offer significant advantages over the previously known devices and methods. The heat exchange catheter offers minimally invasive, quick cooling of the heart. Because no hospital facilities are required to use the present device, it may be deployed on site or in the ambulance, cooling the heart within the critical early stages of ischemia. The apparatus may be used at the onset of ischemia, or during surgery such as while patient is going through percutaneous transluminal coronary angioplasty (PTCA) or other procedures. Cooling can be potentially effective for other organ protection, such as nephropathy or brain ischemia.

DETAILED DESCRIPTION OF THE INVENTION

The embodiments disclosed in this document are illustrative and exemplary and are not meant to limit the invention. Other embodiments can be utilized and structural changes can be made without departing from the scope of the claims of the present invention.

As used herein and in the appended claims, the singular forms "a," "an," and "the" include plural reference unless the context clearly dictates otherwise. Thus, for example, a reference to "a surface" includes a plurality of such surfaces, and a reference to "a lumen" is a reference to one or more lumens and equivalents thereof, and so forth.

A specific embodiment of the heat exchange catheter system of the invention has the following features: a first elongate tubular body 1 having a proximal end and a distal end, and a second elongate tubular body 2 having a proximal end and a distal end, the second elongate tubular body disposed longitudinally within the first elongate tubular body 1. Also provided is a balloon 4 defining a lumen 8 in fluid communication with the first elongate tubular body 1 and the second elongate tubular body 2 so as to form a continuous fluid pathway. The balloon is sealably affixed to the outer surface of the first elongate tubular body and also sealably affixed to the outer surface of the third elongate tubular body. The balloon is shaped and sized so that when inflated, it conforms to (fits snuggly within) the interior of the anatomical structure (the esophagus). Thus when placed within the anatomical structure and inflated, the outer surface of the balloon is at least partially in contact with the inner surface of the anatomical structure. This contact surface provides a heat exchange surface whereby heat may be exchanged between the inner surface of the anatomical structure and interior of the balloon.

As shown in FIG. 1, another specific embodiment of the heat exchange catheter comprises a third elongate tubular body 3 having a proximal end and a distal end, the third elongate tubular body disposed longitudinally within the second elongate tubular body.

In an alternative specific embodiment, as shown in FIG. 6, the third elongate tubular body 3 is disposed in parallel to the first and the second elongate tubular bodies.

In a preferred embodiment, the heat exchange catheter system includes a fluid thermal exchange composition that is pumped into the balloon lumen 8. In use, heat energy passes from the anatomical structure (the esophagus) through the heat exchange surface (the surface of the balloon) into the fluid thermal exchange composition, which may be circulated and cooled by use of a pump and a hear exchanger. As the esophagus is cooled, heat is conducted away from adjacent organs such as the heart, which are also cooled. The rate of cooling may be altered by altering the temperature and flow rate of the thermal exchange composition flowing through the balloon lumen. In certain embodiments, the thermal exchange composition does not need to flow through the system, but may be retained within the balloon.

Figure 5:
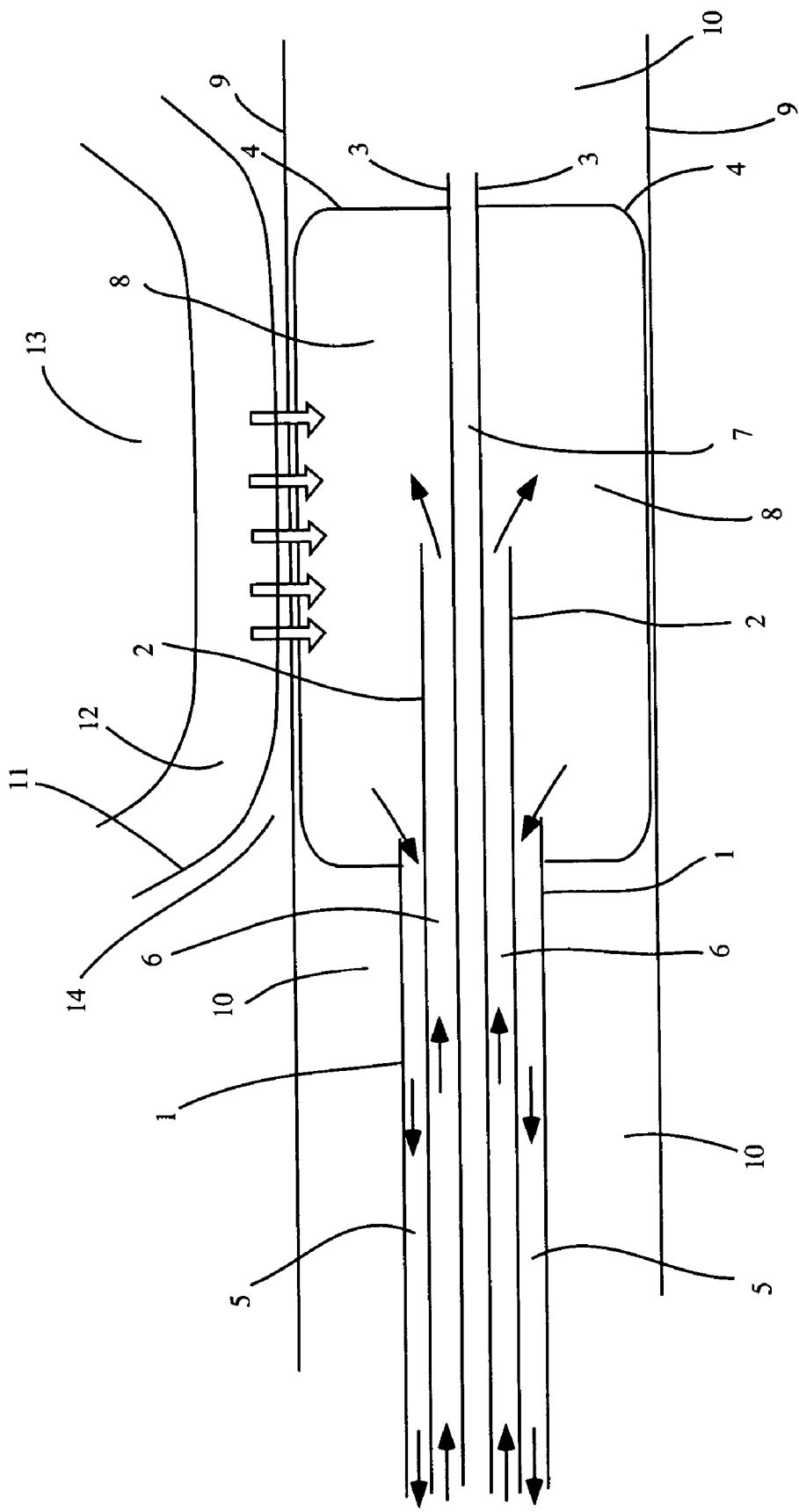
FIG. 5 shows a longitudinal cross-section of an exemplary embodiment of the invention positioned within a body cavity, the body cavity in this instance being the esophagus. The relative position of a part of the heart is also shown. The balloon is shown inflated. Direction of flow is shown by the black arrows. Direction of heat flow is shown by the open arrows.
Figure 8:
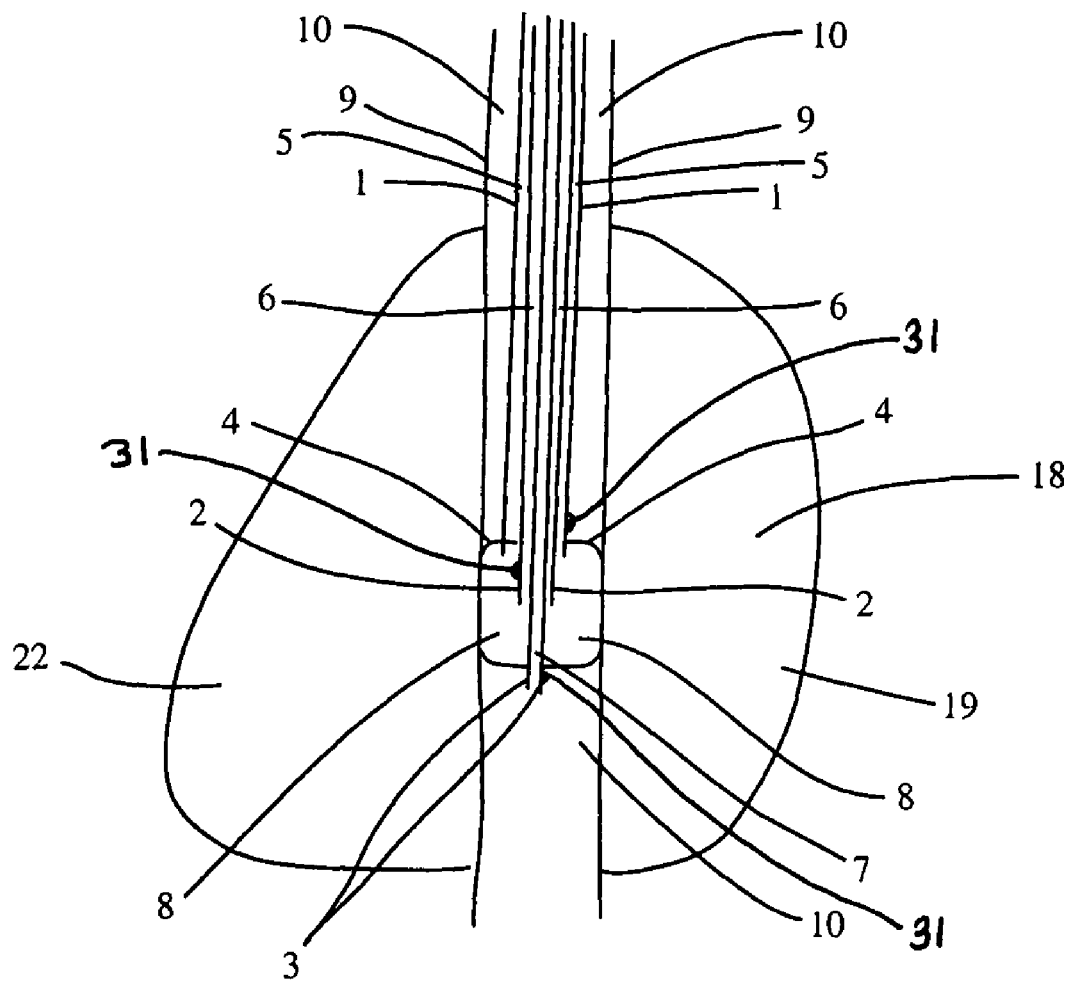
FIG. 8 shows a longitudinal cross-section of an exemplary embodiment of the invention positioned within the esophagus showing the relative position of the device with respect to the heart tissues. The balloon is shown inflated.

As shown in FIG. 5 and FIG. 8, the proximity of the esophagus to the surface of the heart facilitates heat exchange between the two tissues, therefore, the temperature of the myocardium of the heart can be changed by adjusting the temperature of the heat exchange composition in the balloon. The temperature of adjacent body tissues and structures, for example, the left coronary artery and vein, the pulmonary veins, and the vagus nerve, can also be changed. In addition, intra-thoracic fluids located within the thoracic cavities can act as heat-exchange fluids to transfer heat from one organ to another organ.

In one embodiment, the left ventricle of the heart of a subject is cooled using a catheter of the invention positioned within the esophagus of the subject. The catheter may be inserted into the esophagus of the patient through the nose or mouth, followed by temporarily sealing a space surrounding a portion of the catheter within the esophagus wall by inflating the balloon. An anesthetic compound can be administered to the subject's esophagus or larynx to prevent reflexive muscle movements such as the gagging reflex or other muscle spasms. The anesthetic can be administered in a sprayable composition directly onto the surface of the tissue, or by injection into blood vessels or into muscle. A lubricant may generally be used to aid insertion of the device into the esophagus. Visible markings on the outer surface of the catheter can be used to determine the depth to which it has been inserted, and so to help position the distal portion of the device in at a predetermined depth within the esophagus. The markings may refer, for example, to the distance from the site of the incisors of a subject to a site in the esophagus that is adjacent to the subject's heart.

The catheter may have at least one imaging marker (such as a radio-opaque marker) situated at a known position on or within the catheter, for example at either end of the balloon. These markers can be used to view the position of the balloon when inserted into a subject. The marker can be selected from, but is not limited to, radio-opaque compounds, fluorescent compounds, radioactive compounds, and the like.

In certain embodiments, the device may further include an anesthetic or a drug that induces local flaccid paralysis. Such a drug could be incorporated into a gel or other substance applied to the outside of the device. When inserted into the esophagus, the drug would locally anesthetize and/or paralyze the esophagus, thereby making insertion of the device easier and less uncomfortable. Such anesthetics and drugs include, for example, lidocaine and/or ketamine.

The catheter of the invention may employ a heat exchanger positioned in thermal communication with the thermal exchange composition. The heat exchanger can provide heat or remove heat from the thermal exchange composition.

The thermal exchange composition may be a gas, such as, but not limited to, gases used in refrigerant arts, for example, nitrous oxide (Cryo-Chem, Brunswick, Ga.), Freon™, carbon dioxide, nitrogen, and the like. The thermal exchange composition can be a liquid such as saline solution. The thermal exchange composition can be a gel, such as a gel that has a high specific heat capacity. Such gels are well known to those of skill in the art (see, for example, U.S. Pat. No. 6,690,578). Alternatively, a slurry may be used such as a mixture of ice and salt. The thermal exchange composition can be a solid, such as ice or a heat conducting metal such as, but is not limited to, aluminum or copper. An additional embodiment of the invention envisions a combination of different thermal exchange compositions, such as, but is not limited to, a liquid-solid heat exchange combination of saline solution and aluminum metal shaped into fins.

In yet another embodiment of the invention, the thermal exchange composition comprises two or more chemical compositions separately located in the catheter lumens that, when mixed, remove heat from the environment. Examples of such two chemical compositions are ammonium nitrate and water, but are not limited to these compositions. When ammonium nitrate and water are mixed an endothermic reaction occurs and heat is taken up by the reagents in a predictable manner. In yet another embodiment of the invention, the thermal exchange composition comprises two chemical compositions separately located in the catheter lumens that, when mixed, generate heat. Examples of such two chemical compositions are magnesium metal and water, but are not limited to these compositions. When magnesium metal and water are mixed an exothermic reaction occurs and heat is released in a predictable manner. Additional chemical compositions that improve the rate of reaction are known to those of skill in the art.

The various tubular bodies of the heat exchange catheter of the invention can extend proximally outside the body of the patient to connect at its proximal end to equipment used for balloon inflation, for exchange and circulation of thermal exchange composition fluids, and for heating and cooling thermal exchange composition. The catheter tubular bodies 1 and 2 can extend proximally outside the body of the patient to connect at the proximal end to equipment for balloon inflation, pumping of the thermal exchange composition, and heating and cooling of the thermal exchange composition.

The catheter tubular bodies may be constructed of any suitable materials sufficiently flexible so as to be able to follow and conform to the natural shape of the esophagus, but sufficiently stiff to hold its generally linear shape while being pushed into the esophagus.

The balloon 4 can be constructed of materials sufficiently flexible so as to be able to follow and conform to the natural shape of the esophagus, such as latex rubber, elastic, or plastic.

Although the present disclosure generally discusses use of the heat exchange catheter of the invention for the cooling of the heart via the esophagus, the catheter may be further used in a number of other clinically relevant applications. Such applications include, but are not limited to the following: abdominal surgery, cardiac arrest, fever control in critical/intensive care, head injury, hemorrhagic stroke, hypothermia or hyperthermia due to exposure or to trauma, neurological surgery, and vascular surgery.

Various specific embodiments of the heat exchange catheter of the invention are described by the figures as follows:

FIG. 1 shows a schematic longitudinal cross-section of an embodiment of the heat exchange catheter. The catheter comprises three elongated tubular bodies. The first elongated tubular body 1 comprises a proximal end and a distal end and a first lumen 5. The second elongated tubular body 2 is longitudinally positioned within first lumen 5 of the first elongated tubular body 1 and comprises a proximal end and a distal end and a second lumen 6. The third elongated tubular body 3 is longitudinally positioned within second lumen 6 of the second elongated tubular body 2 and 3 comprises a proximal end and a distal end and a third lumen 7. In one embodiment, the third elongated tubular body 3 has a closed distal end. Balloon 4 is attached at at least one attachment place on the exterior of the first elongated tubular body, and at at least one attachment place on the exterior of the third elongated tubular body at or near the distal end. The balloon defines an inflation lumen 8 that is fluidly connected to both lumen 5 and lumen 6. The balloon 8 is shown deflated.

Figure 11:
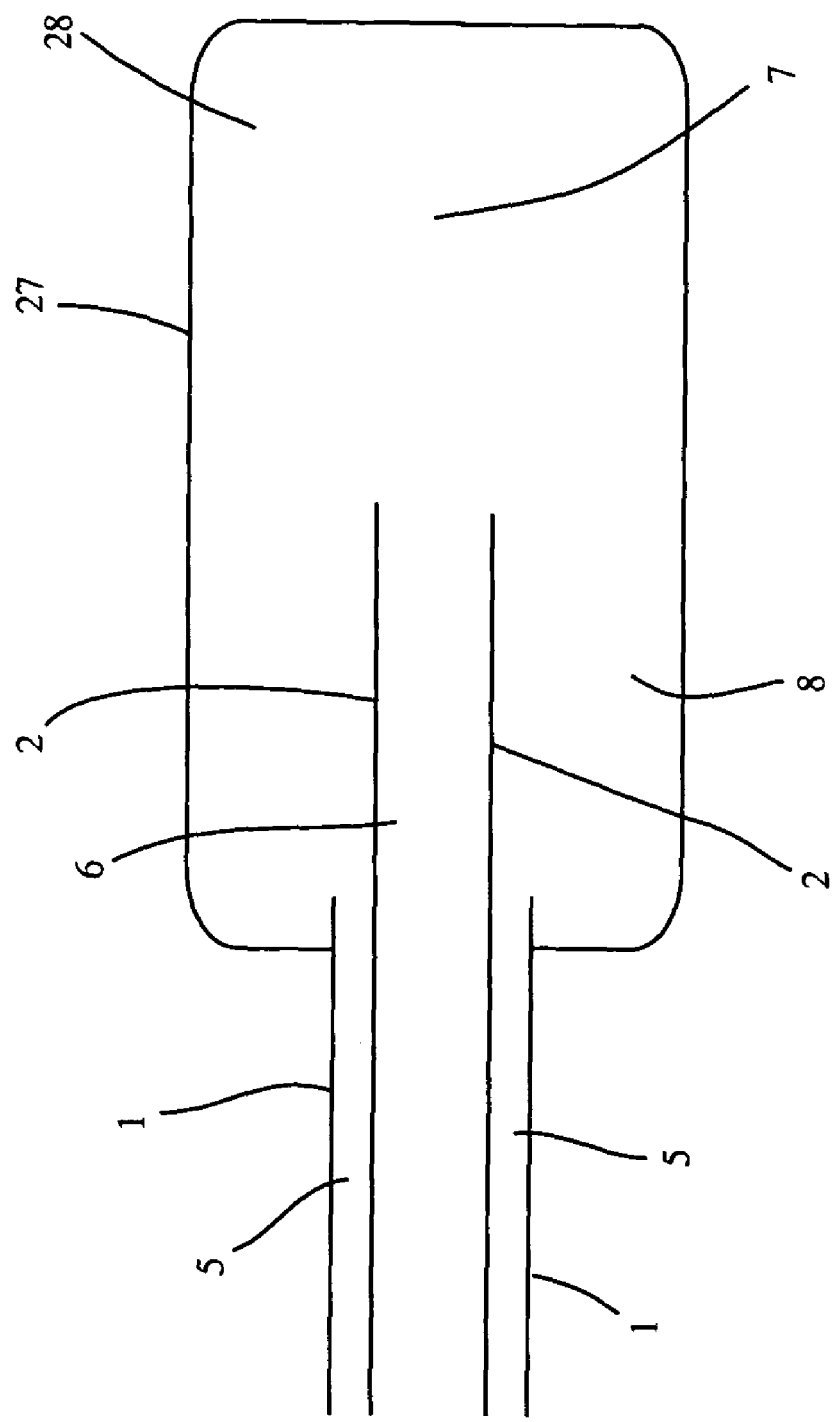
FIG. 11 shows a longitudinal cross-section of an exemplary embodiment of the invention.
Figure 12:
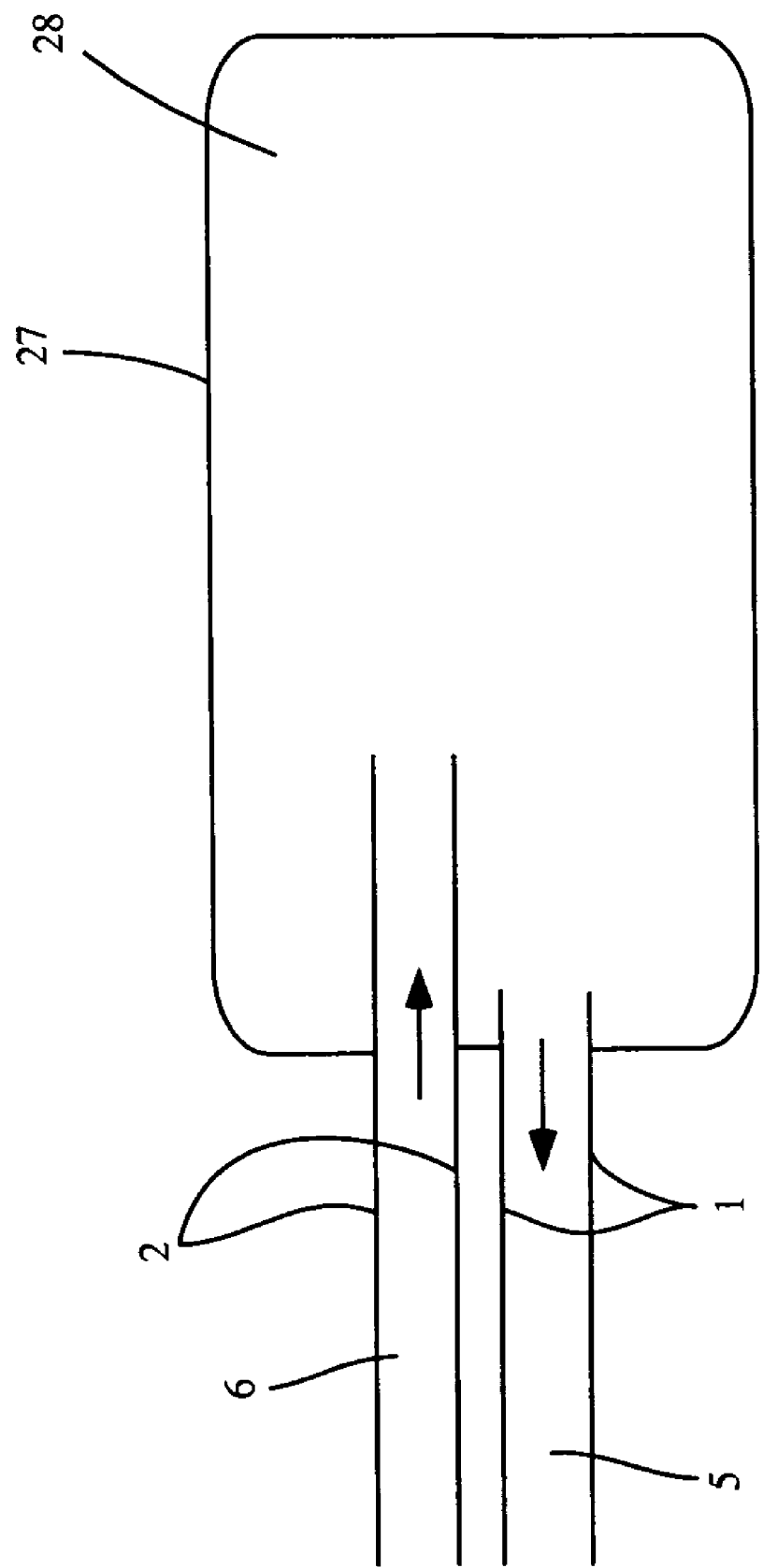
FIG. 12 shows a longitudinal cross-section of an exemplary embodiment of the invention. Direction of flow is shown by the arrows.

The heat exchange catheter may also comprise a saccular body 27 comprising a lumen 28 containing a heat exchange composition that may be cooled or heated (see FIGS. 11 and 12).

In use, the heat exchange catheter is inserted into the esophagus and positioned adjacent to the posterior part of the heart. The balloon is inflated by conduction of a thermal exchange composition under external pressure. This thermal exchange composition enters the balloon lumen 8 via the lumen 6 of the second elongated tubular body 2 and fills the balloon. The thermal exchange composition then exits the balloon lumen 8 via the lumen 5 of the first elongated tubular body 1. The surface of the inflated balloon contacts the inner surface wall of the esophagus and conducts heat from the esophagus wall through the balloon surface to the thermal exchange composition.

The posterior heart myocardium adjacent to the anterior wall of the esophagus is cooled by conduction of heat from the heart to the esophagus. The rate of cooling for an organ of particular mass and size can be determined empirically or by calculation.

The thermal exchange composition can be circulated by pumping the composition through the tubes and balloon of the catheter using a pump. The flow rate of the thermal exchange composition can be adjusted by changing the pumping rate. The thermal exchange composition may be circulated so that it is brought into contact with a heat exchanger device, preferably affixed to the proximal end of the heat exchange catheter. The rate of cooling provided by the device may be controlled by altering the temperature and/or flow rate of the thermal exchange composition.

Figure 2A:
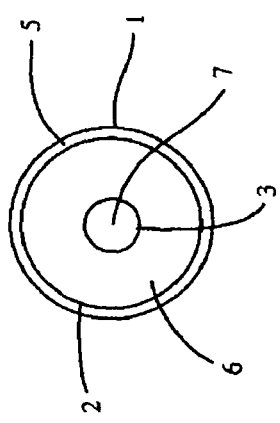
FIGS. 2A, 2B, and 2C show a lateral cross-section from three sections of an exemplary embodiment of the invention.
Figure 2C:
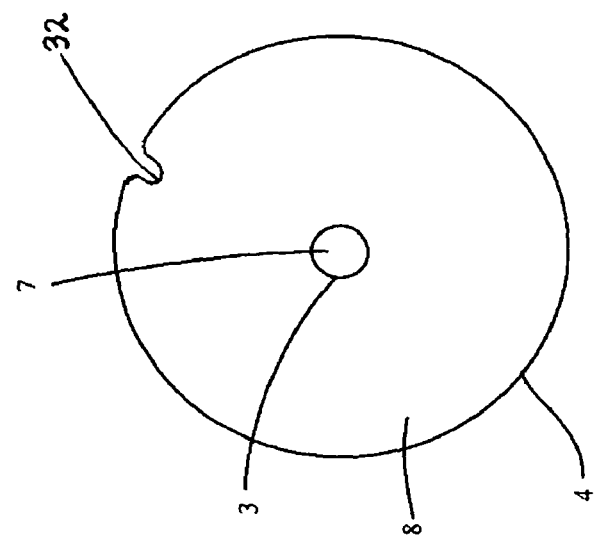
Figure 2B:
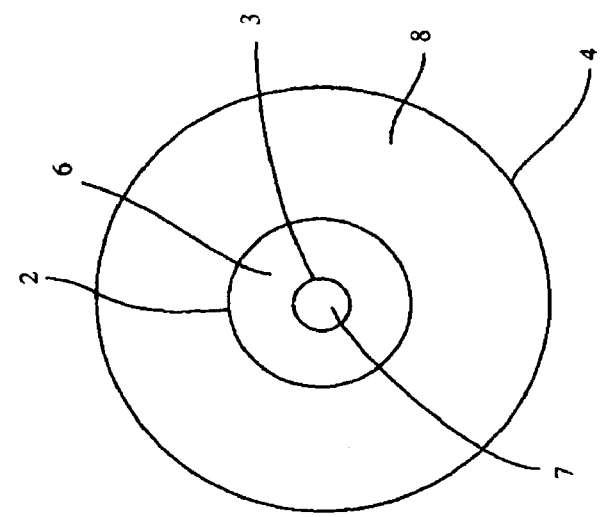

In certain embodiments the cross-sectional area of lumen 6 is larger than the cross-sectional area of lumen 5. The difference in the cross-sectional surface areas of lumen 5 and lumen 6 creates a differential flow rate of the thermal exchange composition. This differential flow rate results in a build-up of pressure in inflation lumen 8, thereby inflating the balloon 4. The balloon inflates until it is constrained by contact with the inside walls 10 of the esophagus 9. Referring to FIG. 2, three transverse cross-sectional representations of the generally elongated tubular catheter are illustrated, FIGS. 2A, 2B, and 2C. FIG. 2A shows the transverse cross-section of the catheter at the proximal end comprising elongated tubular body 1, elongated tubular body 2, and elongated tubular body 3. The catheter also comprises lumen 5, lumen 6, and lumen 7. The cross-sectional area of lumen 5 is less than the cross-sectional area of lumen 6. FIG. 2B shows the transverse cross-section of the catheter at the distal end of tubular body 2 comprising balloon 4, elongated tubular body 2, and elongated tubular body 3. The catheter also comprises lumen 7, lumen 6, and inflation lumen 8. FIG. 2C shows the transverse cross-section of the catheter at the distal end comprising elongated tubular body 3, and balloon 4. The catheter also comprises lumen 7 and inflation lumen 8.

Figure 3:
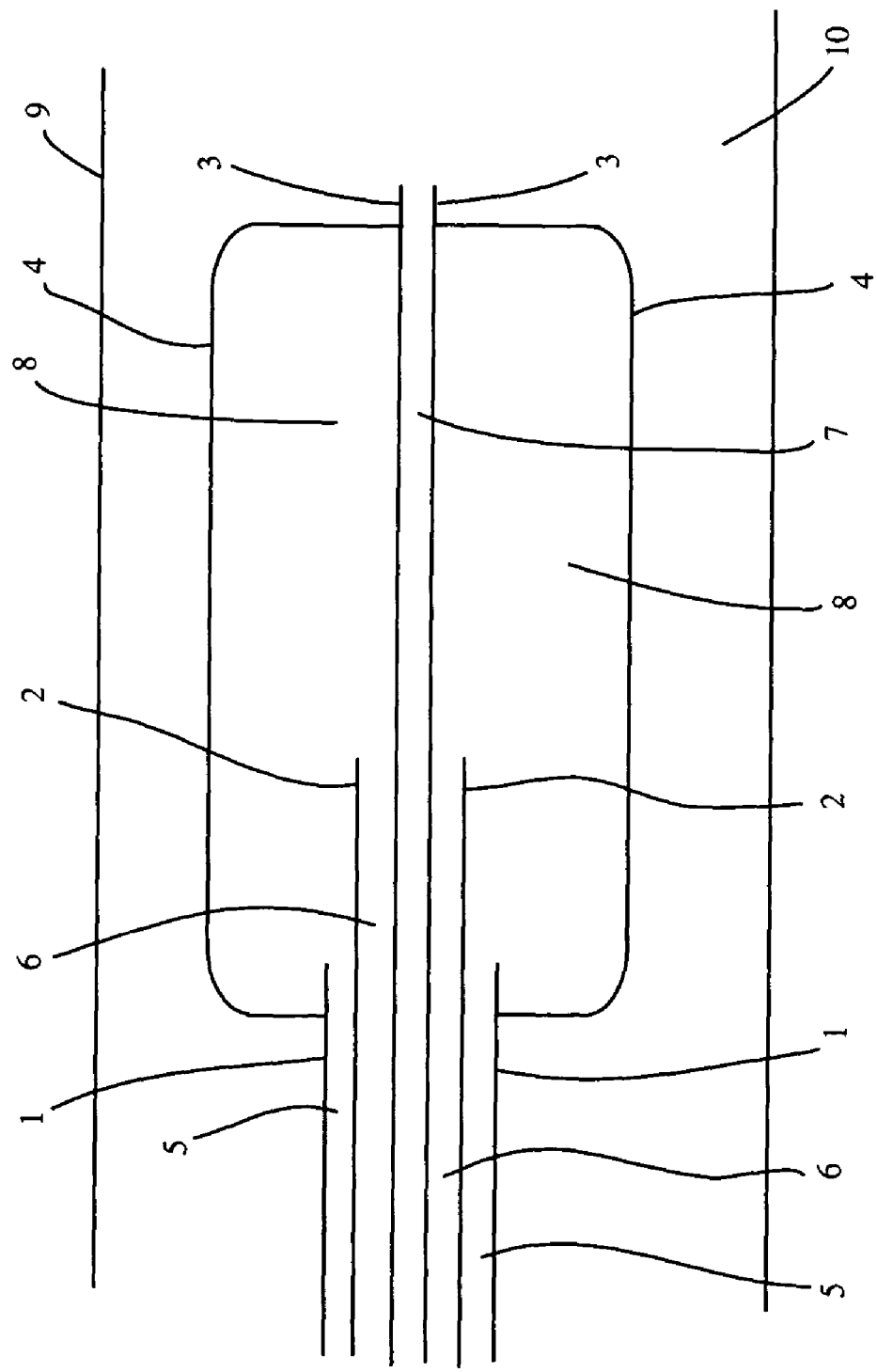
FIG. 3 shows a longitudinal cross-section of an exemplary embodiment of the invention positioned within a body cavity, the body cavity in this instance being the esophagus. The balloon is shown deflated.

Referring to FIG. 3, a generally elongated tubular catheter is illustrated. The catheter is shown within a tubular passage 10 representing the lumen of the esophageal wall 9. The balloon 8 is shown deflated.

Figure 4:
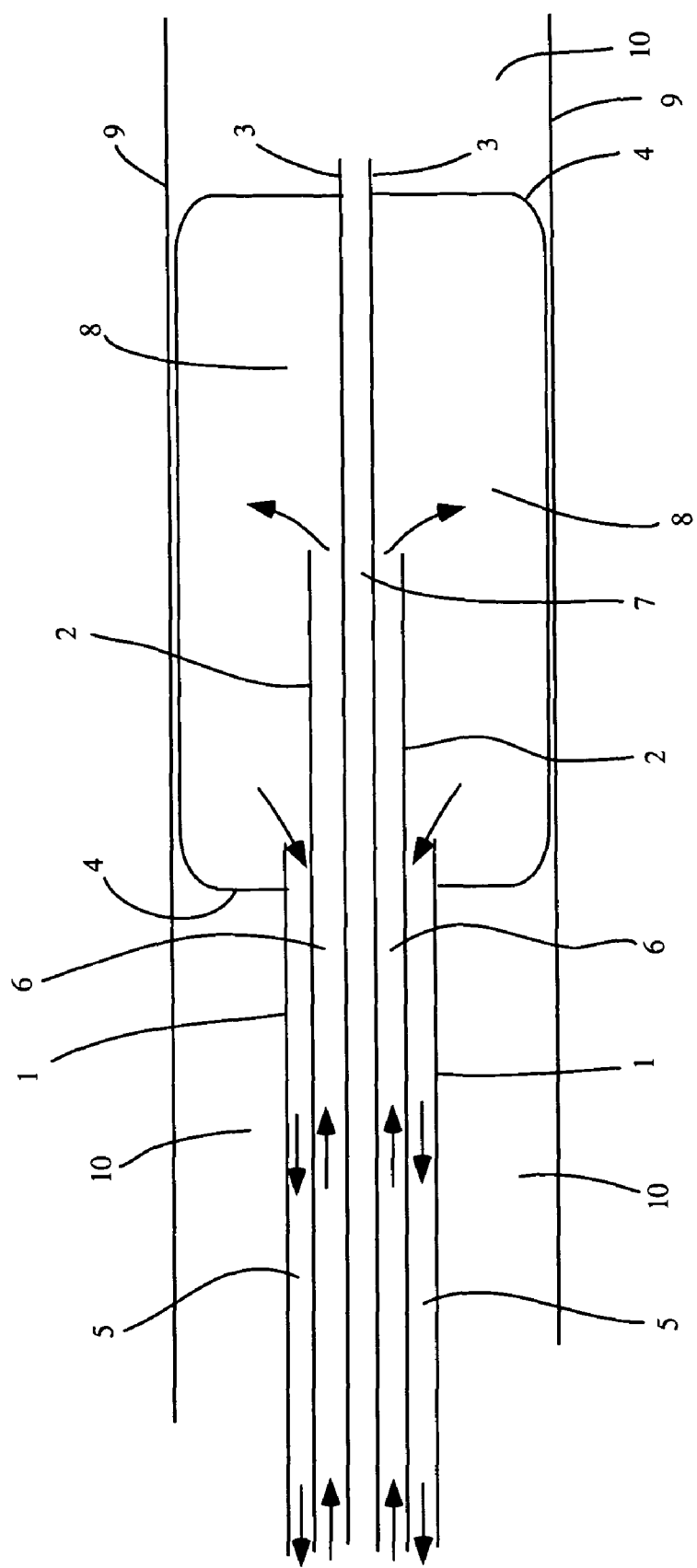
FIG. 4 shows a longitudinal cross-section of an exemplary embodiment of the invention positioned within a body cavity, the body cavity in this instance being the esophagus. The balloon is shown inflated. Direction of flow is shown by the arrows.

Referring to FIG. 4, the catheter is shown within a tubular passage 10 representing the lumen of the esophageal wall 9. Arrows indicate the direction of flow of the heat exchange composition. The balloon 8 is shown inflated.

FIG. 5 shows the inflated balloon 4 positioned within the esophageal lumen 10 relative to the position of the wall of the esophagus 9 and to the external surface of the heart 11 within the thoracic cavity 14. The difference in temperature of the thermal exchange composition compared with that of the heart results in a thermocline across the wall of the esophagus 9 from the myocardium 12 and the surface of the heart 11 to the balloon 4 and the inflation lumen 8. The thermocline is shown in FIG. 5 by open arrows, the arrows pointing in the direction of the heat flow. The result is that heat is transferred from the myocardium to the thermal exchange composition, resulting in a decrease in the temperature of the myocardium.

In other embodiments of the invention the heat exchange catheter may be used to raise the temperature of the myocardium of the heart (or any other organ) above the core temperature, in clinical cases or hypothermia for example. Although the embodiments of this disclosure generally describe devices and methods for cooling the heart, the invention may be also be used to cool or heat organs other than the heart. For example the brain may be cooled to prevent or reduce neurological cell death during brain ischemia, or the kidneys may be cooled to reduce nephropathy.

FIG. 6A shows an embodiment wherein the first and second elongated tubular bodies are not concentric but are separate and parallel. The balloon is attached to the exterior of all three tubes 1, 2, and 3. The thermal exchange composition enters the balloon lumen via the second elongated tubular body 2, and exits the balloon lumen via the first elongated tubular body 1. The inflation lumen 8 of balloon 4 is fluidly connected to lumen 5 and lumen 6. The transverse cross-sectional surface area of lumen 6 is larger than the cross-sectional surface area of lumen 5. An optional guidewire 15 is shown longitudinally positioned in lumen 7.

FIG. 6B shows the transverse cross-sectional representation catheter shown in FIG. 6A. It can be clearly seen that the transverse cross-sectional surface area of lumen 6 is larger than the cross-sectional surface area of lumen 5.

Figure 7:
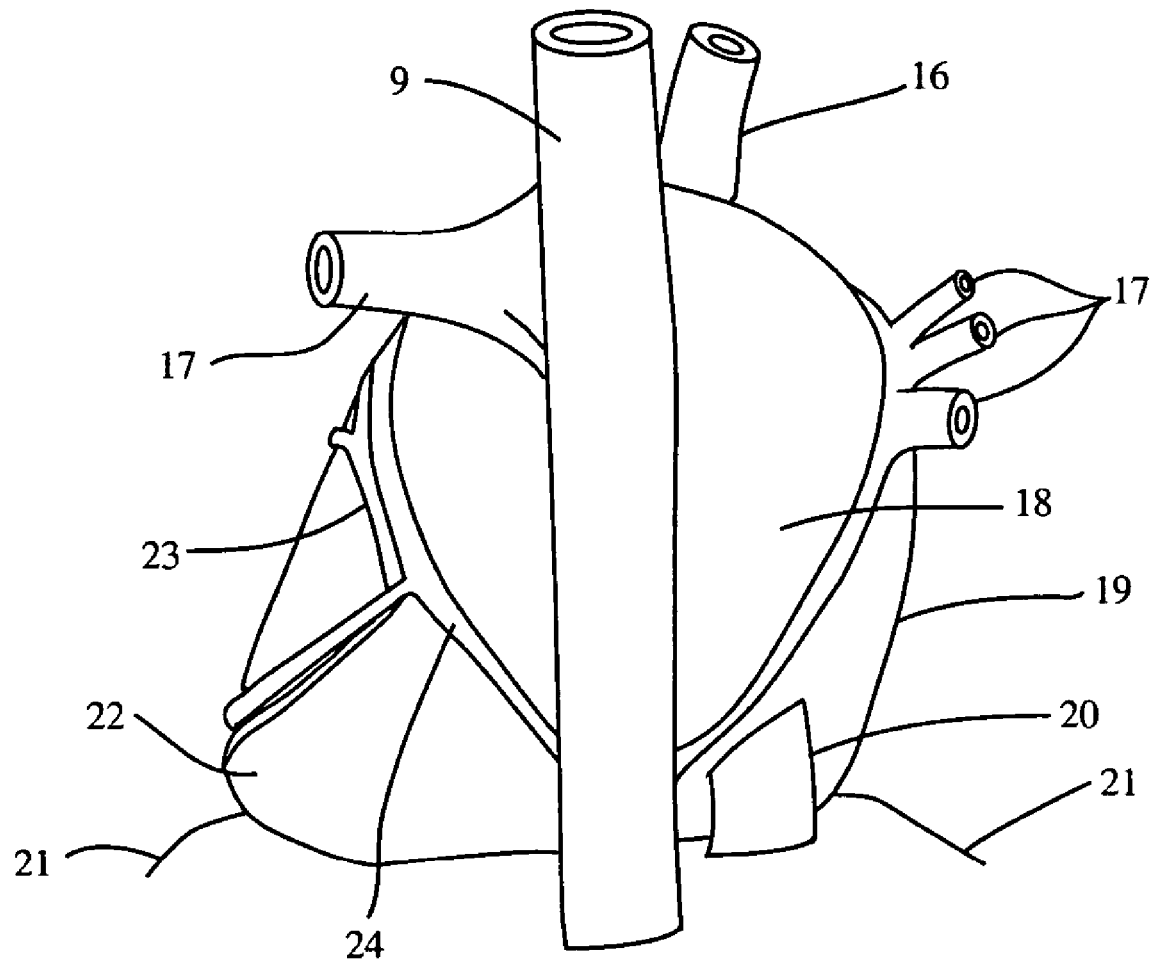
FIG. 7 is an anatomical illustration showing the relative positions of the esophagus, the heart, the major arteries and veins in and around the heart, and the diaphragm.

FIG. 7 shows the anatomical position of the heart and the esophagus 9 within the thoracic cavity in a posterior view. The esophagus 9 is shown to be positioned adjacent to the myocardium of the left ventricle 22, the myocardium of the left atrium 18 and the myocardium of the right atrium 19. Also shown are the superior vena cava 16, the pulmonary veins 17, the inferior vena cava 20, the diaphragm 21, the left coronary artery 23 and the left coronary vein 24.

FIG. 8 shows the position of the catheter of the invention in use with the balloon inflated. Also shown are the relative positions of the esophageal lumen 10, the wall of the esophagus 9, the myocardium of the left atrium 18, the right atrium 19, and the left ventricle 22. An imaging marker 31 (for example, a radio-opaque mark) can be imprinted or placed at any point upon or within the catheter of the invention, for example marks may be positioned upon the distal end of the elongated tubular body 3 or at or near the distal end of elongated tubular body 1. Such markers 31 can be used to visualize the position of the catheter when in use so that the balloon may be properly positioned in proximity to the myocardium.

Figure 9:
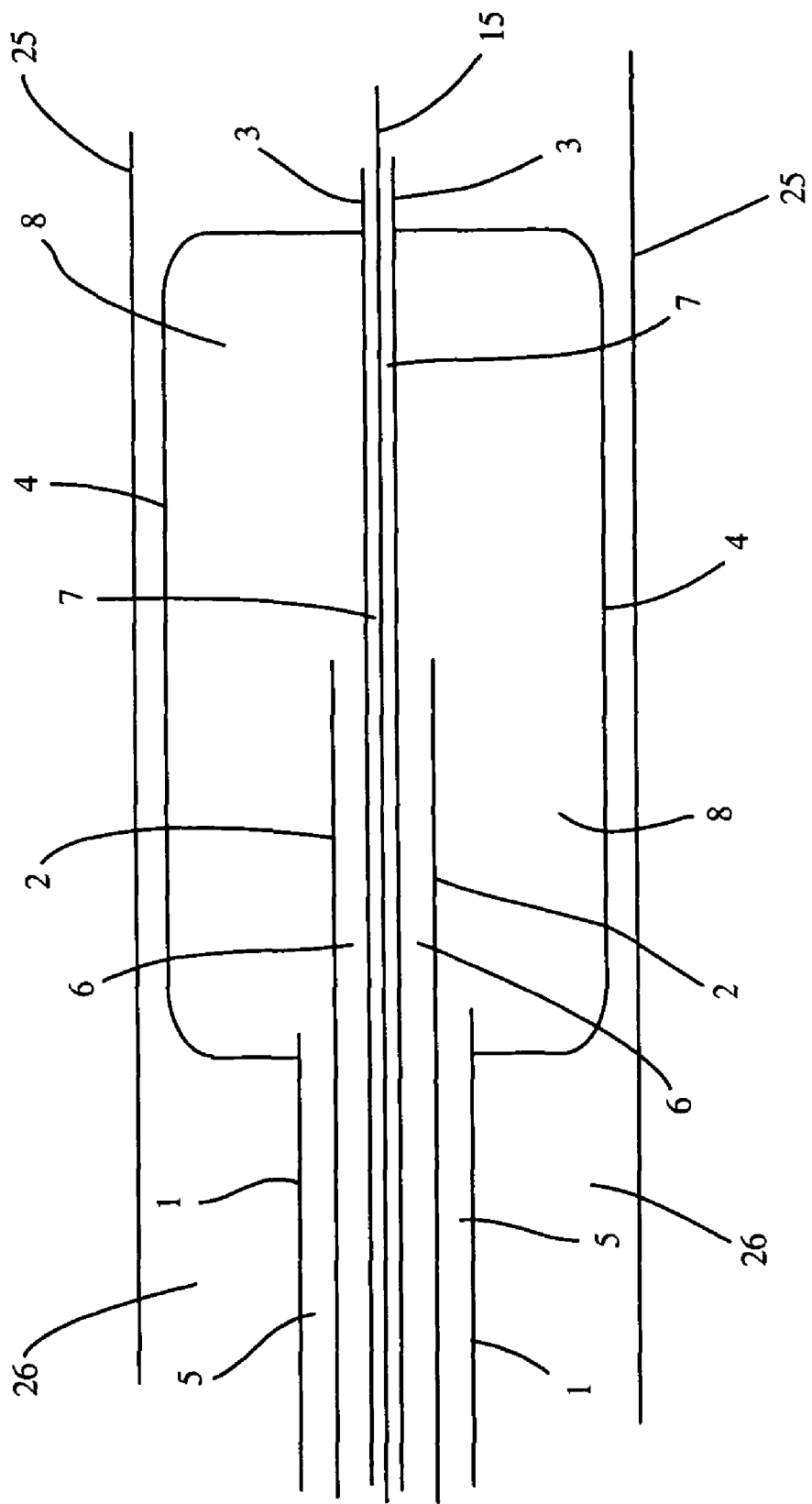
FIG. 9 shows a longitudinal cross-section of an alternative exemplary embodiment of the invention enveloped by a sheath.

Referring to FIG. 9, an alternative embodiment of the invention comprises an additional optional sheath 25. The sheath 25 defines a lumen 26. An elongated tubular catheter of the invention as described above is longitudinally positioned within lumen 26.

Figure 10:
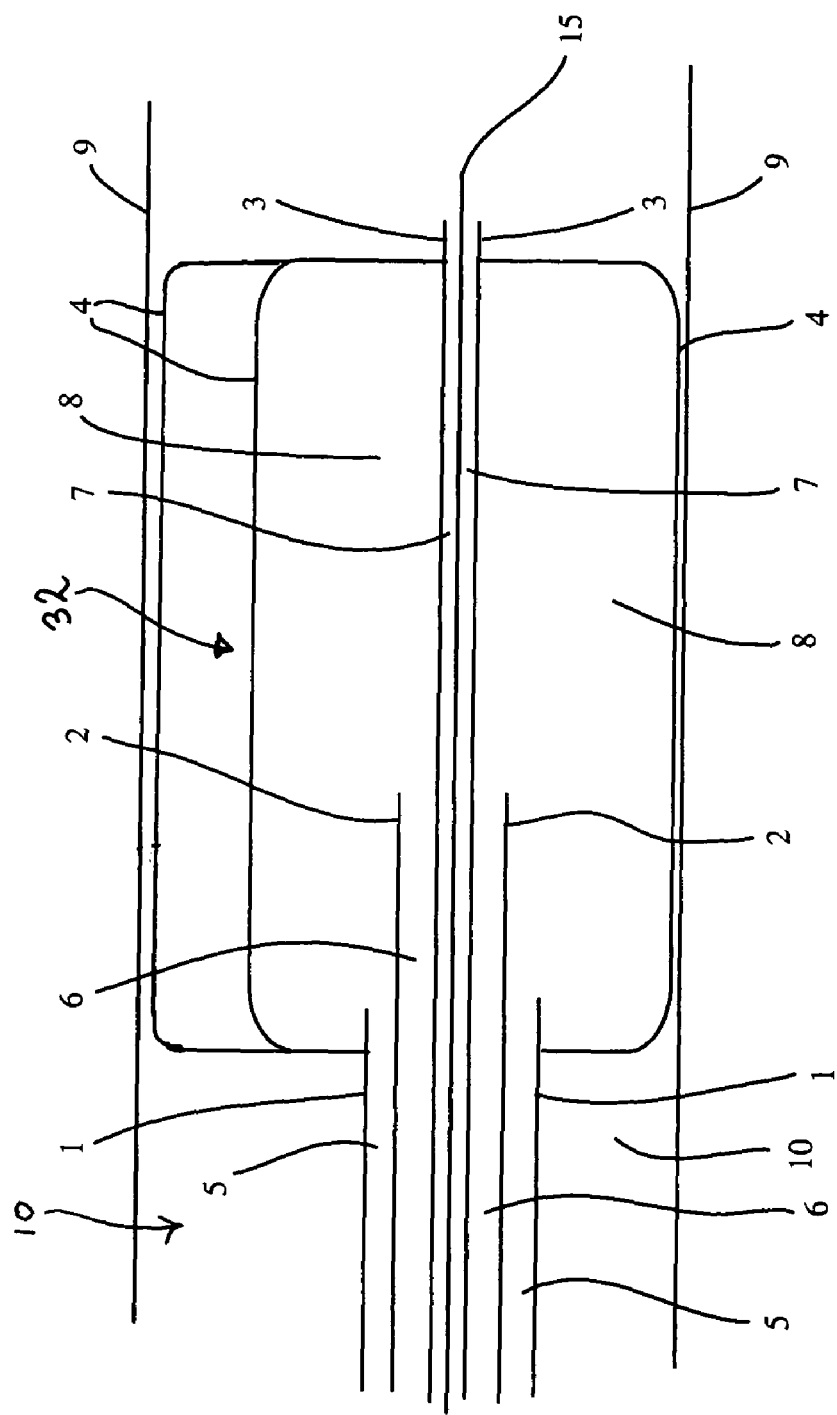
FIG. 10 shows a longitudinal cross-section of an alternative exemplary embodiment of the invention wherein the balloon is asymmetric in shape. The balloon is shown inflated. The invention is shown positioned within the esophagus.

Referring to FIG. 10, an alternative embodiment of the invention comprises an asymmetrical balloon 4. The balloon, when inflated, has a groove 32 disposed longitudinally on its outer surface. The inflated balloon does not completely fill the region of the lumen of the esophagus defined by the groove 32, does not restrict movement of the wall of the esophagus 9 (allowing swallowing), and does not restrict movement of fluids within the lumen of the esophagus 10.

Referring to FIG. 11, an alternative embodiment of the invention is shown wherein the balloon is a saccular body 27. The catheter comprises two elongated tubular bodies. The first elongated tubular body 1 comprises a proximal end and a distal end and a first lumen 5. The second elongated tubular body 2 is longitudinally positioned within first lumen 5 of the first elongated tubular body 1 and comprises a proximal end and a distal end and a second lumen 6. Saccular body 27 defining lumen 28 is attached at at least one attachment place on the exterior of the first elongated tubular body. The lumen 28 of saccular body 27 can contain a heat exchange composition that may be cooled or heated.

Referring to FIG. 12, an alternative embodiment of the invention is shown. The catheter comprises two elongated tubular bodies. The first elongated tubular body 1 comprises a proximal end and a distal end and a first lumen 5. The second elongated tubular body 2 comprises a proximal end and a distal end and a second lumen 6. Saccular body 27 is attached at at least one attachment place on the exterior of the first elongated tubular body and at at least one attachment place on the exterior of the second elongated tubular body.

Calculation of Cooling Rate

Mathematical models of heat exchange during cooling and warming of a subject's internal organs are well known in the art. Such models have been demonstrated as being of use in cardiopulmonary bypass procedures (see, for example, Curtis and Trezek (1985) in *Heat Transfer in Medicine and Biology*, Shitzer and Eberhart (editors), Plenum Publishing Corp., New York, N.Y., volume 2, 261-286; herein incorporated by reference in its entirety).

In addition, heat transfer rates between a target tissue and another intervening tissue can be determined using several mathematical models well know to those of skill in the art. Examples are models such as, but not limited to, steady-state models; one, for example, assumes a model of a single cylinder; another example assumes a model of two cylinders having different dimensions; another example is a transient model of heat transfer that is used to determine cooling or heating rates.

Design of Tubes

One embodiment of the catheter of the invention comprises elongated tubular bodies that have different cross-sectional areas. As is well known in the art, for a device having paired tubes in fluid communication with a balloon, having a different diameter tube that conducts a fluid into the balloon compared with the diameter of a tube that conduct the fluid out of a balloon changes the internal pressure of the inflated balloon, for a given flow rate. To ensure that the balloon inflates and is pressurized when the fluid is circulating within the device, the inflow passage is bigger than the outflow passage.

For the purposes of design of a concentric tubular system, it can be assumed that the inflow passage is disposed concentrically and coaxially within the outflow tube. The cross-sectional area of the inflow tube should be greater than the cross-sectional area of the outflow tube. For example, if "d" is the cross-sectional area of the inflow tube and "D" is the cross-sectional area of the outflow tube then the following equation must be satisfied:

2d>D

For a pair of tubes comprising an inflow tube and an outflow tube that are not coaxial and concentric the relationship between the cross-sectional area of the inflow tube "d" and the cross-sectional area of the outflow tube "D" is represented by the following equation:

d>D

Control of Flow Rate

The flow rate of the heat exchange composition can affect the rate of heat transfer between the outside surface of the heat exchange catheter system and the heat exchange composition in the lumen of the heat exchange catheter system. Flow rate through the catheter of the invention can be adjusted by means well known to those of skill in the art. Examples include, but are not limited to, peristaltic fluid pumps, single or dual valve fluid pumps, manual flow regulators, machine controlled flow regulators, and the like.

Size of Catheter

The catheter of the invention is shaped and sized for placement in a body cavity of a mammalian subject. Examples of such a cavity are body cavities such as, but not limited to, the esophagus, the oral cavity, the nasopharyngeal cavity, the auditory tube and tympanic cavity, the sinus of the brain, the arterial system, the venous system, the larynx, the pharynx, the trachea, the bronchus tubes, the stomach, the duodenum, the ileum, the colon, the rectum, the bladder, the ureter, the ejaculatory duct, the vas deferens, the urethra, the uterine cavity, the vaginal canal, and the cervical canal.

EXAMPLES

The invention will be more readily understood by reference to the following examples, which are included merely for purposes of illustration of certain aspects and embodiments of the present invention and not as limitations.

Example I

Calculation of Heat Transfer in Tissues

Several models have been used by those of skill in the art to determine the rate at which heat is transferred between tissues. In one example, the heat transfer rate between blood and other tissues is calculated using a bio-heat transfer equation. In this example, the bio-heat transfer equation is expressed as:

$$\rho c \frac{\partial T}{\partial t} = q_v + kV^2 T + m_b c_b (T_a - T)$$

Developed Tissue Heat = Energy Heat Source + Conductive Heat Loss + Capacitive Heat Loss and where:
$\rho$ is tissue density in kg m$^{-3}$
c is tissue specific heat at constant pressure in J kg$^{-1}$ °C.$^{-1}$
$c_b$ is blood specific heat at constant pressure in J kg$^{-1}$ °C.$^{-1}$
k is thermal conductivity of the tissue in W m$^{-1}$ °C.$^{-1}$
$m_b$ is blood perfusion rate at a specific arterial size level in kg s$^{-1}$ m$^{-3}$
$q_v$ is volumetric heat generation rate in W m$^{-3}$
t is time in seconds
T is transient tissue temperature in degrees Celsius
$T_a$ is arterial temperature at a specific arterial size level in degrees Celsius The above equation can be understood as the energy balance between the source term and the conductive and capacitive heat loss terms given by k V$^2$ T and $m_b c_b$ ($T_a$-T) respectively. The sum of the energy source and the loss terms gives the specific absorption rate (SAR) denoted by the left hand term and is responsible for the change in temperature of atheroma tissue over time.

The power density source term $q_v$ in the above heat transfer equation comprises contributions from any externally applied power source $q_a$ and the internal power generation term $q_m$ due to metabolic effects within the tissue.

Example II

Calculation of Thermal Exchange Composition Temperature

Three mathematical models were used to determine the theoretical temperature that could cool a target tissue using the heat exchange catheter system of the invention. Two steady-state models and one transient model of heat transfer were used.

The main goal of these calculations was to determine if trans-esophageal cooling could cool down the posterior side of the left ventricle and what temperature the cooling device should be set.

The calculations were done assuming the following parameters:
Tissues were modeled as water
The inner diameter of the esophagus was 20 mm
The thickness the esophageal wall was 5 mm
The thickness of the fibrous tissue between the esophagus and the heart tissue was 8 mm
The thickness of the heart tissue was 10 mm
The temperature of the blood inside the left ventricle was 37.5° Celsius
The heart tissue temperature would cool down to 33° Celsius.

1) Steady-State Models

One Cylinder Model:

This model gave results only for the part of the left ventricle tissue that is the closest to the esophagus.

The model assumes a cylinder of length L, comprising four concentric layers of different compositions with different densities and thermal conductivities. The radii of the three of the layers at their boundaries are given as $r_1$, $r_2$, and $r_3$. The parameters $\rho_B$ (conductivity constant of body tissue) and $\rho_W$ (thermal conductivity of water) are assumed to be constant. The functions determine temperature $T_1$, which is the temperature of the innermost concentric composition layer representing the thermal exchange composition. $T_2$ is the temperature at the boundary of the second and third layer, representing the boundary between the esophagus and the heart. $T_3$ is the temperature at the boundary of the third and fourth layer, representing the boundary between the heart myocardium and the blood in the heart chamber. $q_r$ represents the heat transfer from the centerpoint of first layer to the boundary of the third layer with the fourth layer.

Two heat transfer equations were used:

$$q_r = \frac{T_2 - T_3}{\rho_{T-B}}, \rho_{T-B} = \frac{\ln(r_3/r_2)}{2\pi\rho_W \cdot L} + \frac{1}{\rho_B 2\pi r_3 \cdot L} \quad (1)$$

$$q_r = \frac{T_1 - T_2}{\rho_{C-T}}, \rho_{C-T} = \frac{\ln(r_2/r_1)}{2\pi\rho_W \cdot L} \quad (2)$$

It follows that:

$T_1 - T_2 = \rho_{C-T} q_r$ $T_1 = \rho_{C-T} q_r + T_2$

The parameters used were as follows:
$r_1$=0.010 m
$r_2$=0.023 m
$r_3$=0.030 m
L=0.100 m
$T_2$=306 K
$T_3$=310.5 K
$\rho_B$=2000 kg m$^3$
$\rho_W$=0.6 W/K·m $T_1$ was calculated as 292.4 K or 19.4° C.

It was therefore determined that the temperature of the cooling device had to be set up to 19° Celsius to ensure that the left ventricle tissue temperature remained at 33° Celsius.

Two Cylinder Model:

This model gave a result only for the posterior side of the left ventricle.

The model assumes that two cylinders of different diameters $D_1$ and $D_2$ are adjacent to each other; there is a gap (Inter) between the outer surface of the two cylinders. The longitudinal center point of each cylinder is separated by a distance w. The functions determine temperature $T_2$, which is the temperature of the smaller of the two cylinders representing the thermal exchange composition. $T_1$ is the temperature at the surface of the second cylinder, representing the surface the heart. q represents the heat transfer.

$$q = S\rho(T_1 - T_2), S = \cosh-1\frac{2\pi L}{\frac{(4w^2 - D_1^2 - D_2^2)}{2D_1 D_2}}$$

-continued $$T_2 = T_1 - \frac{q}{S\rho}$$

The parameters used were as follows:
$D_1$=0.048 m
$D_2$=0.025 m
L=0.100 m
Inter=0.005 m
w=0.0415 m
T1=306 K
$\rho_W$=0.6 W/K·m $T_2$ was calculated as 288 K or 15° C.

It was therefore determined that the temperature of the cooling device had to be set up to 15° Celsius to ensure that the temperature of the posterior side of the left ventricle remained at 33° Celsius.

2. Transient Model

This model gave a result only for the part of the left ventricle tissue that is the closest to the esophagus. The heat transfer equation derivative was used to determine the time for the temperature to change ($\Delta T$). Q is the heat transferred; M is the mass of the tissue; $C_W$ is the energy released per degree change per unit mass; $T_B$ represents the temperature of the blood; $T_C$ represents the temperature of the catheter thermal exchange composition; and $T_\infty$ represents the temperature of the left ventricle tissue.

$$C_W M \frac{dT}{dt} = Q, M = \left[\frac{(0.03)^2}{2} - \frac{(0.01)^2}{2}\right] \times \pi \times 0.1 \times 1000 = 0.06283 \text{ kg}$$

It follows that $$C_W M \frac{\delta T}{\delta t} = \delta Q$$

$\delta Q = \delta Q_B + \delta Q_C = q_B + q_C$ $$q_B = \left(\frac{T - T_B}{\rho_{T-B}}\right)$$

$$q_C = \left(\frac{T_C - T}{\rho_{T-C}}\right)$$

$$\delta T \approx T_\infty - T = \frac{\Delta T}{C_W M} \cdot \left[\left(\frac{T - T_B}{\rho_{T-B}}\right) + \left(\frac{T_C - T}{\rho_{T-C}}\right)\right]$$

$$\Delta T = \frac{C_W M}{\left(\frac{T - T_B}{\rho_{T-B}}\right) + \left(\frac{T_C - T}{\rho_{T-C}}\right)}[T_\infty - T]$$

The parameters used were as follows:
$T_B$=310.5 K
$T_C$=288 K
$T_\infty$=306 K
M=0.06283 kg
$C_W$=4185 J/K/kg $\Delta T$ was calculated as 116.24 seconds or ≈2 minutes It was determined that if the temperature of the cooling device was set to 15° Celsius, it would take 2 minutes to cool down the closest section of the left ventricle tissue from 37.5° to 33° Celsius.

Example III

Cooling of the Heart in an Experimental Animal

A catheter according to the invention was used in a large-animal model procedure as disclosed below.

A pig, with a mass of between 30 and 35 kg, was anaesthetized, paralyzed, and prepared for the procedure. Two thermocouple flexible implantable probes were used to measure the temperature of the anterior and posterior sections of the left ventricle. A third esophageal temperature probe also measured esophageal temperatures. In addition, a rectal thermometer measured basal body temperature.

The temperature probes are very small, 0.64 mm in diameter. These temperature probes were placed into the right coronary artery (anterior) and left circumflex branch (posterior) via a percutaneous approach through the femoral artery.

Markers on the probe and the temperature probes helped determine the position of the probe in relation to the heart and the location of the temperature probes.

A 0.5 inch diameter clear tubing sheath was used to open the mouth and airway of the pig prior to insertion of the heat exchange catheter system of the invention. The heat exchange catheter system was inserted in the esophagus of the animal through the oralpharyngeal pathway and positioned as close to the heart as possible. Saline solution was kept in a bucket filled with ice to keep the solution cold and was pumped into the heat exchange catheter system via a simple fishtank pump. The temperature of the saline in the bucket was approximately 40° Fahrenheit (approximately 4-5° C.); data were collected from the four thermometers, every two minutes for one hour.

The catheter had two radiolabeled markers affixed to at least one of the elongate tubular bodies. One of the radiolabeled markers was affixed using epoxy glue at or near the distal end of elongate tubular body 3 disclosed in FIG. 1. The other radiolabeled marker was affixed using epoxy glue at or near the distal end of elongate tubular body 2 disclosed in FIG. 1. The second elongate tubular body of the catheter was connected in fluid communication to the outlet of the fishtank pump. The first elongate tubular body was connected in fluid communication to an evacuation tube. The evacuation tube was connected in fluid communication with the inlet of the fountain pump. A manual flow regulator was affixed to the evacuation tube that could be used to adjust the pressure of a thermal exchange composition in the elongate tubular bodies and the balloon.

The catheter was introduced into the pharynx and esophagus of the anaesthetized pig using typical clinical intubation techniques well known to those of skill in the art. The external surface of an elongate tubular body that can be used as a sheath was lubricated with a biocompatible lubricant. The internal diameter of the lumen of the sheath was larger than the external diameter of the heat exchange catheter system.

The position of the catheter was also be monitored using an angiographic system. The radiolabeled markers were detected using the angiographic system. The catheter was positioned in the esophageal lumen relative to the target region by noting the location of the radiolabeled markers observed using the angiographic system.

In this example, the target region was the myocardium of the heart and the thermal exchange composition was saline.

The catheter was filled with cold saline solution at a temperature of approximately 4-5° Celsius.

The experimental procedure and observations were continued for approximately 60-70 minutes with continuous circulation of the saline and continuous monitoring of the temperature of the esophagus, of the posterior coronary artery, of the anterior coronary artery, and of the rectal body. The procedure was continued at least until the posterior coronary arterial temperature was approximately 5° Fahrenheit below the temperature of the posterior coronary artery at the start of the procedure.

Figure 13:
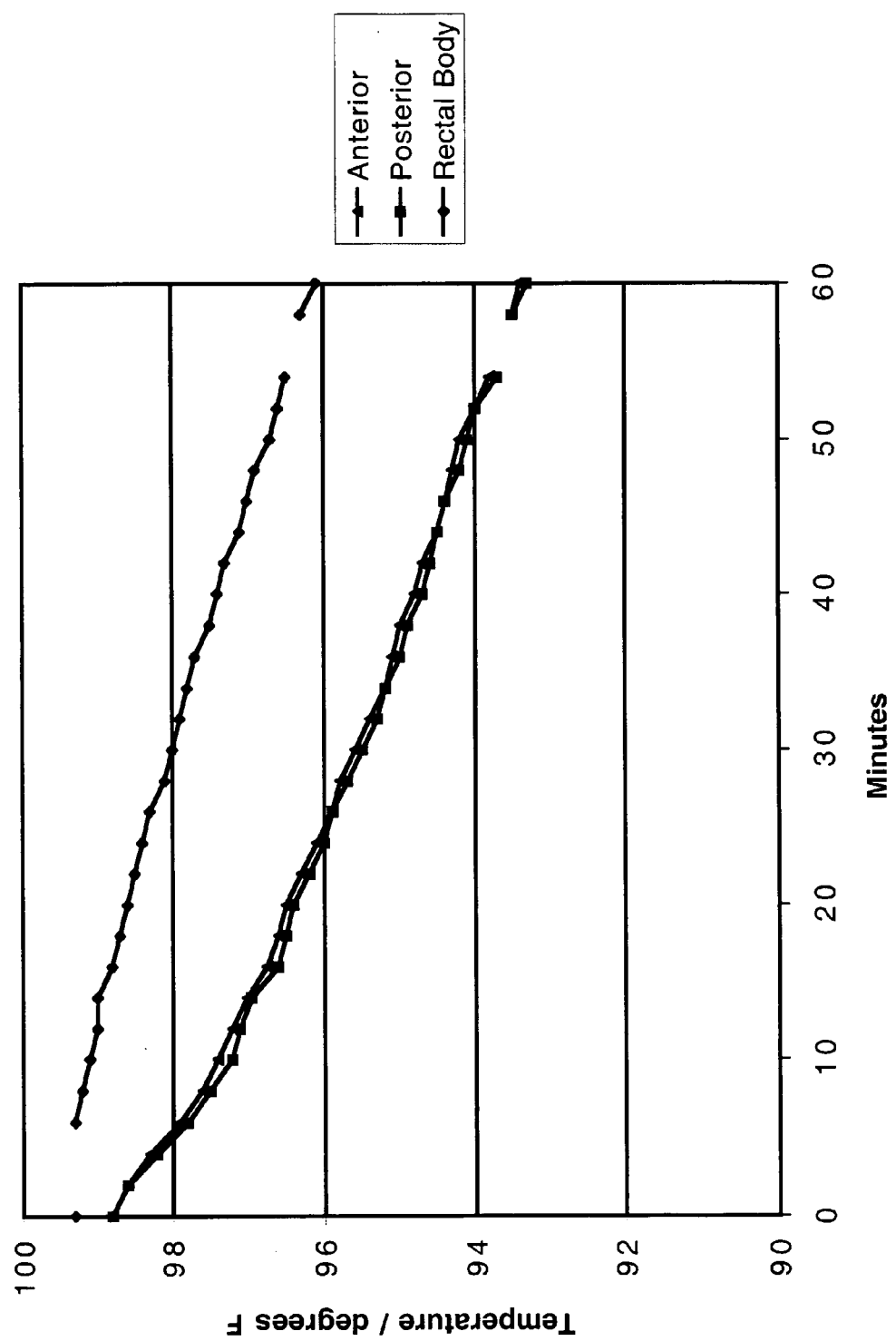
FIG. 13 shows a graph of data from an animal experiment. The temperature of the anterior coronary artery (▲), the posterior coronary artery (■), and the rectal body (♦), are shown. The data graph shows that the heart was cooled by at least 5.5° Fahrenheit (approximately 3° Celsius) over a period of 60 minutes using a heat exchange catheter of the invention.
Figure 14:
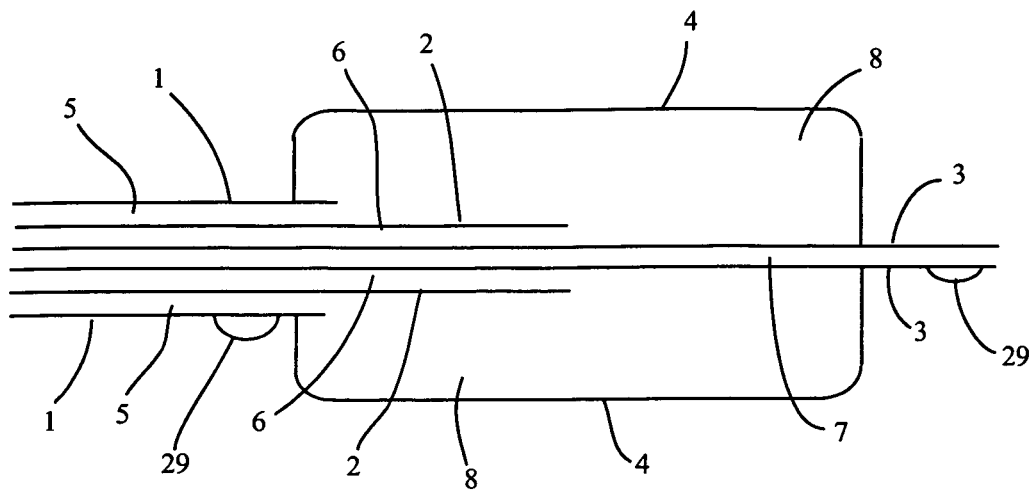
FIG. 14 shows a longitudinal cross-section of an alternative exemplary embodiment of the invention showing position of a transducer.
Figure 15:
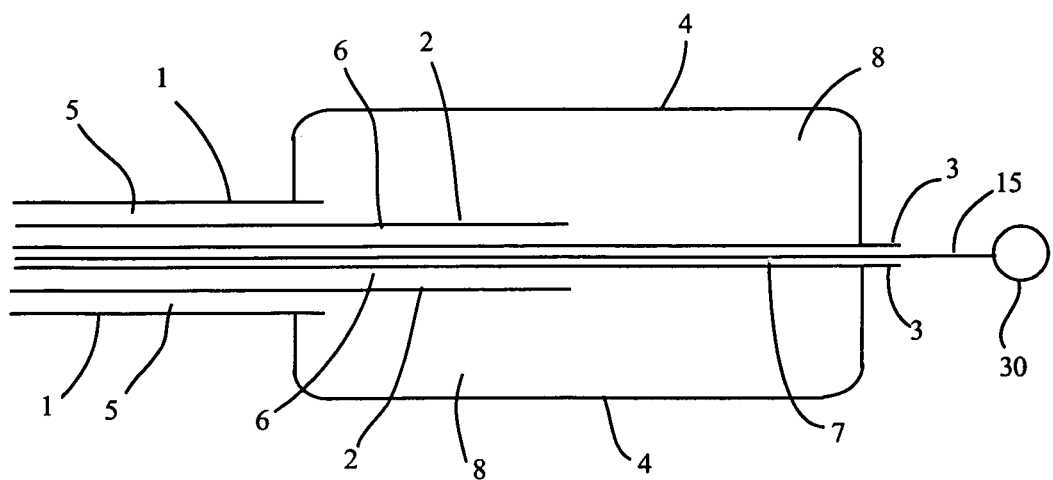
FIG. 15 shows a longitudinal cross-section of an alternative exemplary embodiment of the invention showing position of a digestible composition.

The temperature data from the experiment are shown in Table 1. The data are also plotted as a graph in FIG. 13.

TABLE 1

Transesophageal Cooling of the Heart

| Time | Anterior | Posterior | Esophageal | Rectal Body |
|------|----------|-----------|------------|-------------|
| 0 | 98.8 | 98.8 | No data | 99.3 |
| 2 | 98.6 | 98.6 | No data | No data |
| 4 | 98.3 | 98.2 | No data | No data |
| 6 | 97.9 | 97.8 | No data | 99.3 |
| 8 | 97.6 | 97.5 | 59.8 | 99.2 |
| 10 | 97.4 | 97.2 | 61.4 | 99.1 |
| 12 | 97.2 | 97.1 | 62.7 | 99 |
| 14 | 97 | 96.95 | 63.5 | 99 |
| 16 | 96.75 | 96.6 | 64.2 | 98.8 |
| 18 | 96.6 | 96.5 | 64.1 | 98.7 |
| 20 | 96.5 | 96.4 | 64.3 | 98.6 |
| 22 | 96.3 | 96.2 | 61 | 98.5 |
| 24 | 96.1 | 96 | 58.8 | 98.4 |
| 26 | 95.9 | 95.9 | 58 | 98.3 |
| 28 | 95.8 | 95.7 | 57.4 | 98.1 |
| 30 | 95.6 | 95.5 | 57.4 | 98 |
| 32 | 95.4 | 95.3 | 57.3 | 97.9 |
| 34 | 95.2 | 95.2 | 58.2 | 97.8 |
| 36 | 95.1 | 95 | 58.2 | 97.7 |
| 38 | 95 | 94.9 | 57.5 | 97.5 |
| 40 | 94.8 | 94.7 | 57.7 | 97.4 |
| 42 | 94.7 | 94.6 | 58 | 97.3 |
| 44 | 94.5 | 94.5 | 57.8 | 97.1 |
| 46 | 94.4 | 94.4 | 57.9 | 97 |
| 48 | 94.3 | 94.2 | 58.4 | 96.9 |
| 50 | 94.2 | 94.1 | 58.8 | 96.7 |
| 52 | 94 | 94 | 57.6 | 96.6 |
| 54 | 93.8 | 93.7 | 56.1 | 96.5 |
| 56 | No data | No data | No data | No data |
| 58 | 93.5 | 93.5 | 54.6 | 96.3 |
| 60 | 93.4 | 93.3 | 54.1 | 96.1 |

Note: Temperature is in degrees Fahrenheit

The data show that the temperature of the esophagus was cooled by the saline thermal exchange composition. The temperature of the esophageal probe was between 64.3° Fahrenheit (approximately 18° C.) at 20 minutes after starting the procedure and 54.1° Fahrenheit (approximately 12° C.) after one hour. Thirty minutes after cooling of the esophagus began, the temperature of the posterior coronary artery was 3.3° Fahrenheit (approximately 1.83° Celsius) lower than at the start of the experiment. Sixty minutes after cooling of the esophagus began, the temperature of the posterior coronary artery was 93.3° Fahrenheit (34° Celsius), and therefore 5.5° Fahrenheit (approximately 3° Celsius) lower than at the start of the experiment. This rate of cooling was confirmed by the temperature readings from the anterior coronary artery (93.4° Fahrenheit at 60 minutes) indicating that the effect was not localized to the posterior region of the heart. The data therefore show that both the anterior and posterior regions of the heart had been cooled by a similar degree.

The data therefore shows that the heat exchange catheter of the invention can be used to cool the heart at at least a rate of 3° Celsius per hour and that the decrease in temperature of the heart was achieved at a similar rate to previous methods of cooling.

The results of the above experiments were confirmed by repeat experiment.

Example IV

Use in Human Subjects

A catheter of the invention may be used to cool the myocardium of the human subject. The subject may have been anaesthetized and paralyzed. Alternatively, the subject may have undergone a cardiovascular trauma and is conscious or unconscious. A medical professional, such as a paramedic or a trained physician, can optionally anaesthetize the pharynx and the esophagus using a transient anesthetic. The medical professional can then introduce a standard intubator into the oral cavity and then the pharynx. The catheter of the invention can be then introduced into the esophagus of the subject through the intubator and positioned using a predetermined method. The method can comprise the steps of noting where a printed set of lines align with a part of the subject's anatomy, for example, the lower incisors.

In an alternative use, the catheter can be introduced through the nasal passageway, the upper part of the pharynx, and then to the esophagus.

The procedure of this invention can be performed very rapidly for emergency use. The catheter of this invention can be reused on the same patient, if needed or desired, shortly after the first use, even though the catheter can be of a disposable type.

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

We claim:

1. A heat exchange catheter system for cooling a target organ, the heat exchange catheter system adapted for placement within an anatomical structure of a subject, comprising: (a) a first elongate tubular body (1) having a proximal end and a distal end, (b) a second elongate tubular body (2) having a proximal end and a distal end, (c) a balloon (4) defining a lumen (8) in fluid communication with both the first elongate tubular body (1) and the second elongate tubular body (2) so as to form a continuous fluid pathway, further comprising a third elongate tubular body (3) having a proximal end and a distal end, the third elongate tubular body disposed longitudinally within the second elongate tubular body, and wherein the balloon is sealably affixed to the outer surface of the first elongate tubular body and sealably affixed to the outer surface of the third elongate tubular body, the lumen (8) further comprising a thermal exchange composition, wherein the thermal exchange composition is disposed within the continuous fluid pathway formed by the second elongate tubular body (2), the first elongate tubular body (1), and the balloon lumen (8) and wherein the thermal exchange composition is selected from the group consisting of a solid, a gel, a liquid, and a gas, and (d) a transducer (29), and wherein the balloon (4), when inflated, has a longitudinally disposed groove (32) upon its outer surface, wherein the groove (32) is not in contact with the first elongate tubular body (1) and the balloon (4) is adapted to conform in shape and size to the interior of the anatomical structure such that when placed within the anatomical structure and inflated, the outer surface of the balloon is at least partially in contact with the inner surface of the anatomical structure providing a heat exchange surface by which heat is exchanged between the anatomical structure and interior of the balloon, and whereby the target organ adjacent to the anatomical structure is thereby cooled.

2. The heat exchange catheter system of claim 1 further comprising a guidewire disposed longitudinally within the third elongate tubular body, the guidewire having a proximal end and a distal end.

3. The heat exchange catheter system of claim 2 further comprising a digestible composition (30) affixed at or near the distal end of the guidewire.

4. The heat exchange catheter system of claim 1 wherein the second elongate tubular body is disposed longitudinally within the first elongate tubular body 1.

5. The heat exchange catheter system of claim 1 wherein the subject is a human subject, wherein the anatomical structure is the esophagus, and the target organ is the heart.

6. The heat exchange catheter system of claim 1 wherein the balloon is shaped and sized for placement in the anatomical structure selected from the group consisting of: the esophagus, the oral cavity, the nasopharyngeal cavity, the auditory tube and tympanic cavity, the sinus of the brain, the arterial system, the venous system, the larynx, the trachea, the bronchus, the stomach, the duodenum, the ileum, the colon, the rectum, the bladder, the ureter, the ejaculatory duct, the vas deferens, the urethra, the uterine cavity, the vaginal canal, and the cervical canal.

7. The heat exchange catheter system if claim 1 wherein the target organ is selected from the group consisting of: the myocardium of the heart, the lungs, the thymus, the thyroid, the liver, the pancreas, the kidney, the uterus, the ovary, the testis, the prostate, and the brain.

8. The heat exchange catheter system of claim 1 wherein the balloon conducts heat from the anatomical structure to the thermal exchange composition.

9. The heat exchange catheter system of claim 1 further comprising an ultrasound transducer affixed thereto.

10. The heat exchange catheter system of claim 1 further comprising a guide sheath (25) fitted over at least a portion of the first elongate tubular body.

11. The heat exchange catheter system of claim 1, wherein the target organ is cooled at a rate of between about 0.5° C./hour and 30° C./hour.

12. The heat exchange catheter system of claim 1, wherein the target organ is cooled at a rate of between about 2.0° C./hour and 10° C./hour.

13. The heat exchange catheter system of claim 1, wherein the target organ is cooled at a rate of between about 5° C./hour to about 3° C./hour.

14. The heat exchange catheter system of claim 1, wherein the target organ is cooled at a rate of between about 0.5° C./30 minutes and 30° C./30 minutes.

15. The heat exchange catheter system of claim 1, wherein the target organ is cooled at a rate of between about 2.0° C./30 minutes and 10° C./30 minutes.

16. The heat exchange catheter system of claim 1, wherein the target organ is cooled at a rate of between about 2° C./30 minutes to about 5° C./30 minutes.

17. A method of altering the temperature of the myocardium of the heart in a subject, the method comprising the steps of: placing a heat exchange catheter system into the esophagus of a subject, wherein the heat exchange catheter system is adapted for placement within an anatomical structure of a subject, and comprises (a) a first elongate tubular body (1) having a proximal end and a distal end, (b) a second elongate tubular body (2) having a proximal end and a distal end, (c) a transducer (29), (d) a marker (31), and (e) a balloon (4) defining a lumen (8) in fluid communication with both the first elongate tubular body (1) and the second elongate tubular body (2) so as to form a continuous fluid pathway, further comprising a thermal exchange composition within balloon lumen (8), wherein the thermal exchange composition flows within the continuous fluid pathway formed by the second elongate tubular body (2), the first elongate tubular body (1), and the balloon lumen (8), and wherein the balloon (4), when inflated, has a longitudinally disposed groove (32) upon its outer surface, wherein the groove (32) is not in contact with the first elongate tubular body (1) and the balloon (4) is adapted to conform in shape and size to the interior of the anatomical structure such that when placed within the anatomical structure and inflated, the outer surface of the balloon is at least partially in contact with the inner surface of the anatomical structure providing a heat exchange surface by which heat is exchanged between the anatomical structure and interior of the balloon, and whereby the target organ adjacent to the anatomical structure is thereby cooled; and circulating the thermal exchange composition within the continuous fluid pathway, whereby the myocardium of the heart is cooled.

18. The method of claim 17 wherein the temperature of the myocardium of the heart is altered at a rate of between about 0.5° C./hour and 30° C./hour.

19. The method of claim 17 wherein the temperature of the myocardium of the heart is altered at a rate of between about 3° C./hour and 5° C./hour.

* * * * *